US012796753B2

(12) United States Patent
McBride et al.

(10) Patent No.: US 12,796,753 B2
(45) Date of Patent: Nov. 17, 2026

(54) PERSONAL PROTECTIVE EQUIPMENT ADAPTER SYSTEM FOR USE WITH MEDICAL DEVICES AND METHODS OF MAKING AND USING SAME

(71) Applicants: Mark T. McBride, Coronado, CA (US); John Roughneen, Dennis, MA (US); Phillip Salvatori, Salem, OR (US)

(72) Inventors: Mark T. McBride, Coronado, CA (US); John Roughneen, Dennis, MA (US); Phillip Salvatori, Salem, OR (US)

( * ) Notice: Subject to any disclaimer, the term of this patent is extended or adjusted under 35 U.S.C. 154(b) by 0 days.

(21) Appl. No.: 19/353,705

(22) Filed: Oct. 9, 2025

(65) Prior Publication Data

US 2026/0033569 A1 Feb. 5, 2026

Related U.S. Application Data

(63) Continuation-in-part of application No. 18/945,673, filed on Nov. 13, 2024, now Pat. No. 12,538,951.

(60) Provisional application No. 63/600,148, filed on Nov. 17, 2023.

(51) Int. Cl.
*A61B 90/00* (2016.01)
*A41D 13/11* (2006.01)

(52) U.S. Cl.
CPC .......... *A41D 13/1153* (2013.01); *A61B 90/37* (2016.02); *A61B 2090/365* (2016.02)

(58) Field of Classification Search
CPC ................ A41D 13/1153; A61B 90/37; A61B 2090/365
See application file for complete search history.

(56) References Cited

U.S. PATENT DOCUMENTS

| | | | | |
|---|---|---|---|---|
| 11,857,378 B1 * | 1/2024 | Bojarski | ................ | A61B 90/37 |
| 2016/0331059 A1 * | 11/2016 | Basson | .................. | A42B 3/222 |
| 2017/0216099 A1 * | 8/2017 | Saladino | ................ | A42B 1/247 |

* cited by examiner

*Primary Examiner* — Robert J Michaud
(74) *Attorney, Agent, or Firm* — James R. McDaniel

(57) ABSTRACT

Systems, methods, and other embodiments for a personal protective equipment ("PPE") adapter system for use with an augmented/virtual/mixed reality ("AR") devices, including an AR system having an AR viewing device and a headband operatively connected to the AR viewing device, a PPE adapter system, and a PPE hood operatively connected to the PPE adapter system, wherein the PPE hood includes a face shield, wherein the face shield is removably connected to the PPE adapter system.

16 Claims, 25 Drawing Sheets

PERSONAL PROTECTIVE EQUIPMENT ADAPTER SYSTEM FOR USE WITH MEDICAL DEVICES AND METHODS OF MAKING AND USING SAME

CROSS-REFERENCE TO RELATED APPLICATIONS

This application is a continuation-in-part of U.S. patent application Ser. No. 18/945,673, filed on Nov. 13, 2024 which claims benefit of U.S. Patent Application 63/600,148, filed on Nov. 17, 2023, the disclosures of which are hereby incorporated by reference in their entirety to provide continuity of disclosure to the extent such disclosures are not inconsistent with the disclosure herein.

FIELD OF THE INVENTION

The present invention is generally related to a personal protective equipment ("PPE") adapter system for use with medical devices such as augmented/virtual/mixed reality ("AR") devices and light devices. The system would securely hold the PPE to existing AR/VR/MR headset and lighting solutions. The system would allow the AR devices and lighting devices to operate in surgical environments where a face shield is required.

BACKGROUND OF THE INVENTION

Prior to the present invention, as set forth in general terms above and more specifically below, it is known that AR solutions for existing industry applications do not require full PPE or even protective face shields. In the surgical environment where full face coverings are required, the ability to maintain adequate performance of the spatial imaging system has proven to be a challenge. In particular, cameras are calibrated without the requirement to be able to image through an additional substrate such as a face shield. This is a challenge specifically for the center camera of the spatial imaging system of the AR device. Therefore, it would be desired if the PPE was equipped with an adapter that did not adversely affect the spatial imaging system, specifically the center camera of the spatial imaging system, while the PPE and the spatial imaging system were being used during a medical procedure.

It is a purpose of this invention to fulfill these and other needs in the employing a spatial imaging system with PPE during a medical procedure art in a manner more apparent to the skilled artisan once given the following disclosure.

The preferred PPE adapter system for use with AR devices and lighting devices, according to various embodiments of the present invention, offers the following advantages: ease of use; lightness in weight; the ability to use the AR device in conjunction with a face shield; the ability to use the adapter system on a variety of AR devices; portability; ease of attachment of the adapter to the AR device; ease of removal of the adapter from the AR device; and reduced cost. In fact, in many of the preferred embodiments, these advantages are optimized to an extent that is considerably higher than heretofore achieved in prior, known systems and methods for employing a spatial imaging system and a lighting system with PPE during a medical procedure.

BRIEF DESCRIPTION OF THE DRAWINGS

The above-mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which.

DETAILED DESCRIPTION OF THE PREFERRED EMBODIMENTS OF THE INVENTION

In order to address the shortcomings of the prior, known systems and methods for employing a spatial imaging system and lighting systems with PPE during a medical procedure, it would be desirable if the spatial imaging system, particularly the AR device, and the lighting system was equipped with an adapter that did not adversely affect the spatial imaging system and/or the lighting system, specifically the center camera of the spatial imaging system, while the PPE and the spatial imaging system and/or lighting system were being used during a medical procedure.

PPE Adapter System for Use with a First AR Device

Figure 1:
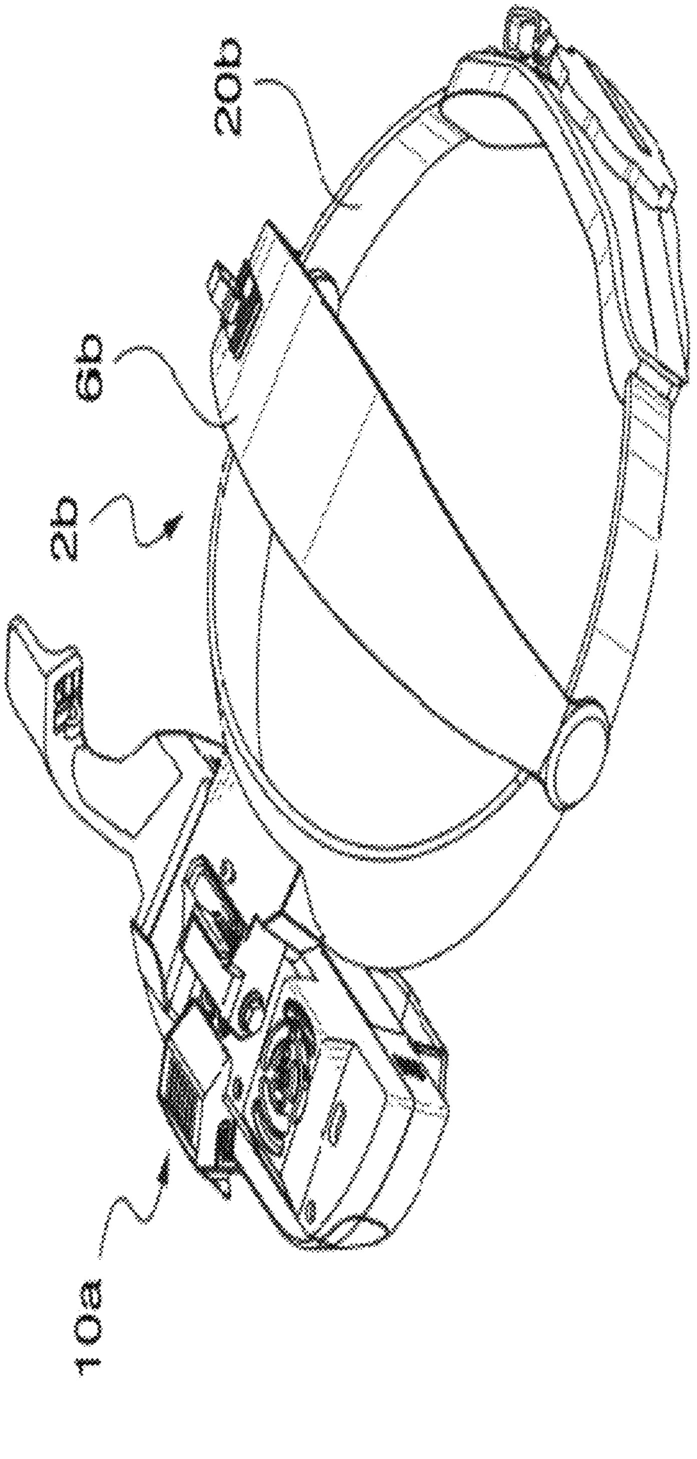
FIG. 1 (Prior Art)
FIG. 1 is an isometric, top view of one embodiment of a first AR device, according to the prior art.
Figure 2:
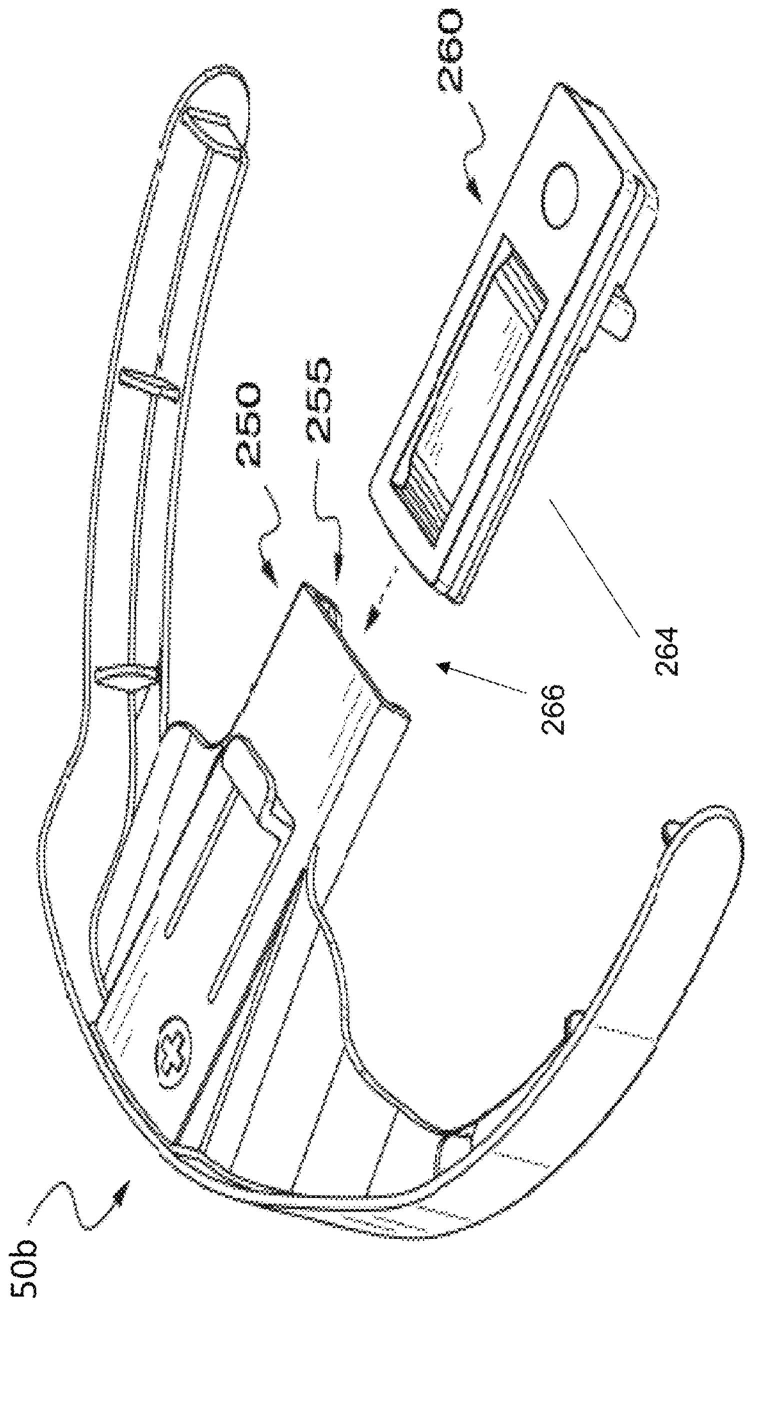
FIG. 2 is an isometric, top view of a PPE adapter system for use with the first AR device, constructed according to an embodiment of the present invention.

Referring now to FIGS. 1-8, there is illustrated another embodiment of a personal protective equipment ("PPE") adapter system 50*b* for use with another model of an augmented reality ("AR") device 2*b*. As shown in FIG. 1, there is illustrated one embodiment of another conventional AR device 2*b*, according to the prior art. Typically, this another AR device 2*b* includes, in part, most of the components as discussed above with respect to AR device 2*a*. However, AR device 2*b* also includes head gear 6*b*, front camera 10*a*, headband 20*b* (FIG. 1), and adapter 50*b* (FIG. 2).

Figure 3:
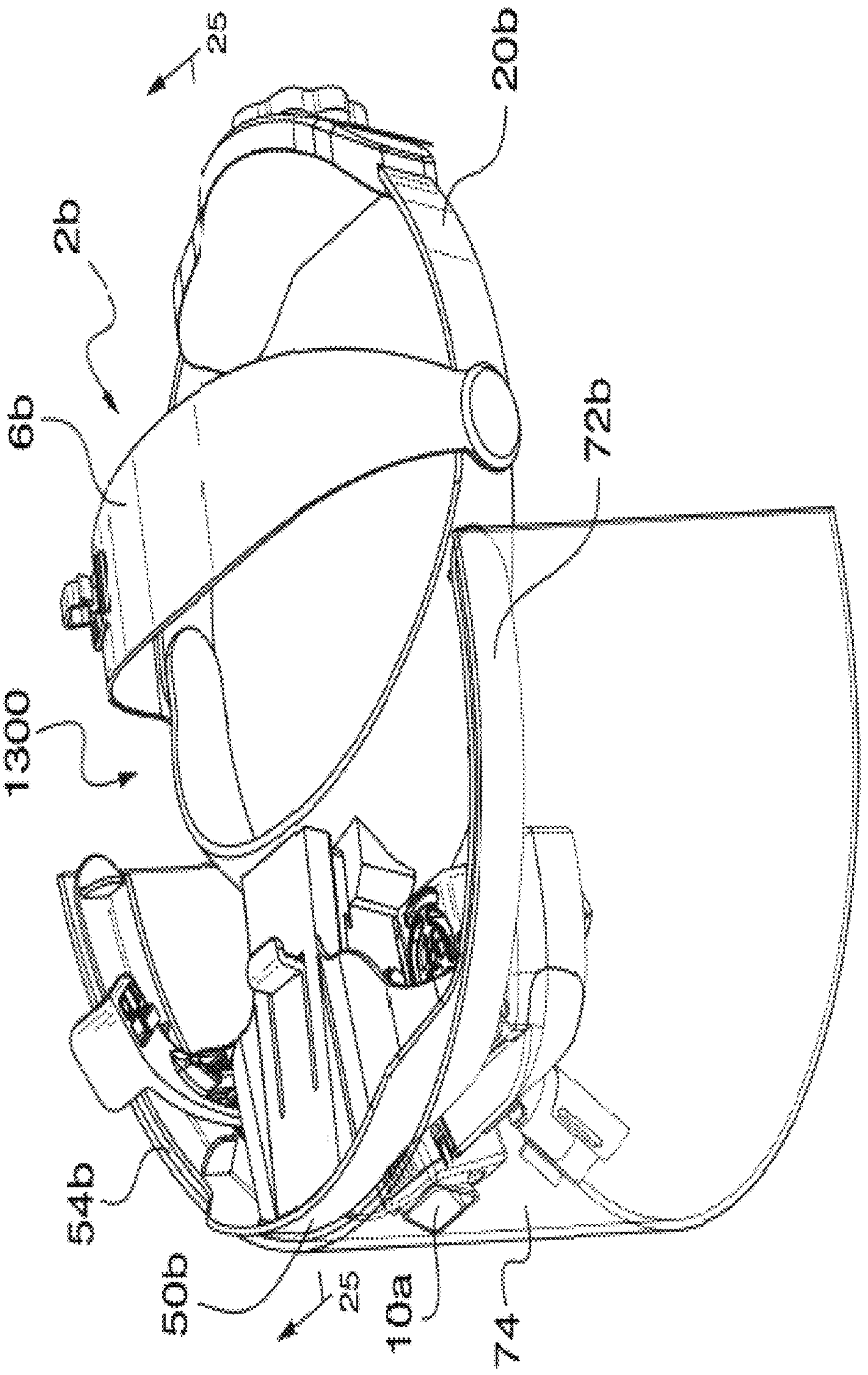
FIG. 3 is a schematic, side view of the face shield being attached to the PPE adapter system for use with the first AR device, constructed according to an embodiment of the present invention.
Figure 4:
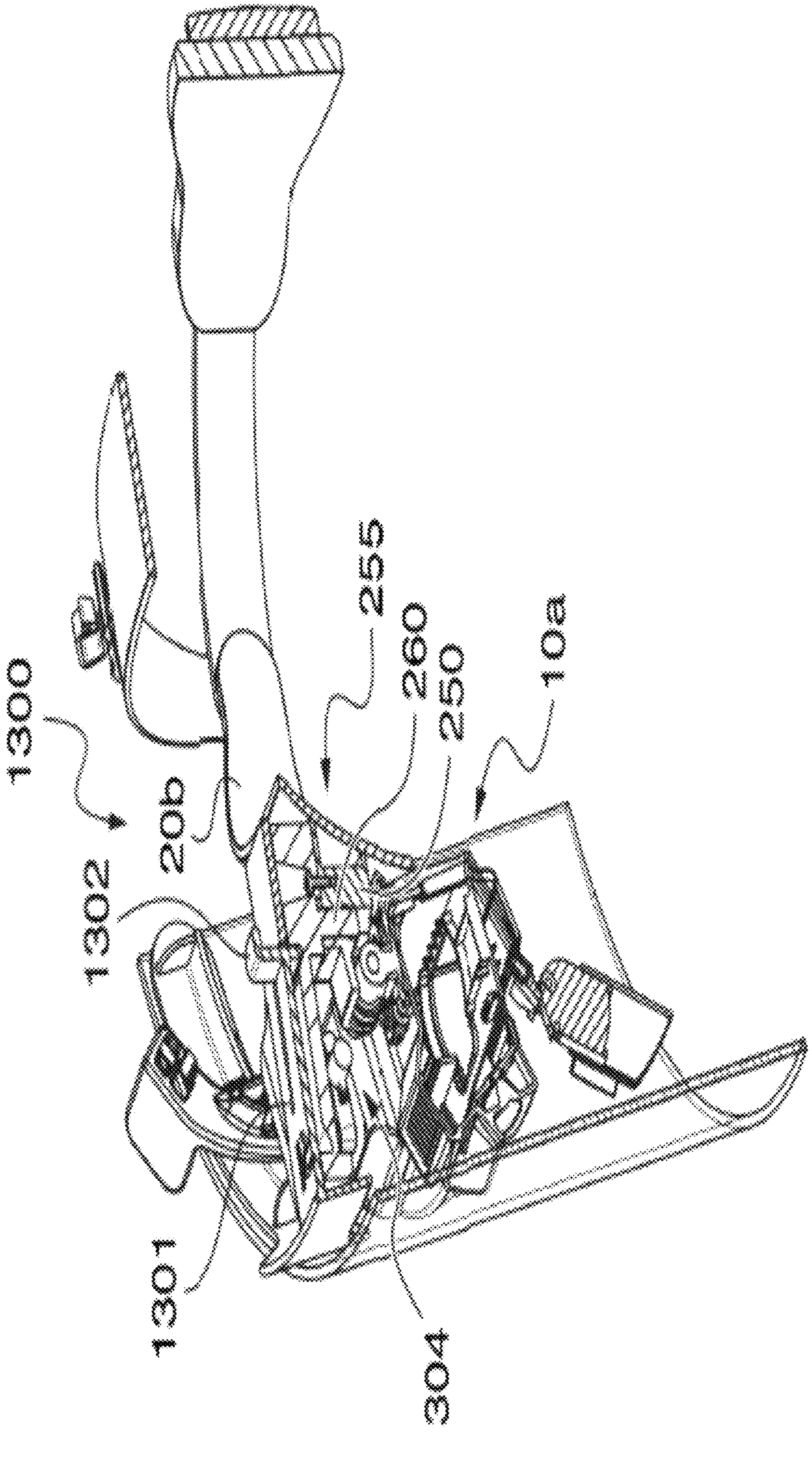
FIG. 4 is a schematic cut-away view of the face shield being attached to the PPE adapter system for use with the first AR device taken along lines 25-25 in FIG. 3, constructed according to an embodiment of the present invention.

With respect to FIGS. 3 and 4, there are illustrated a sliding adapter mount 250 that will allow PPE adapter system 50*b* to be removably attached to AR device 2*b*. In particular, sliding adapter mount 250 includes, in part, extension 255. Preferably, sliding adapter mount 250 is constructed of any suitable durable, UV resistant, heat resistant, lightweight, high strength polymeric material.

Figure 5:
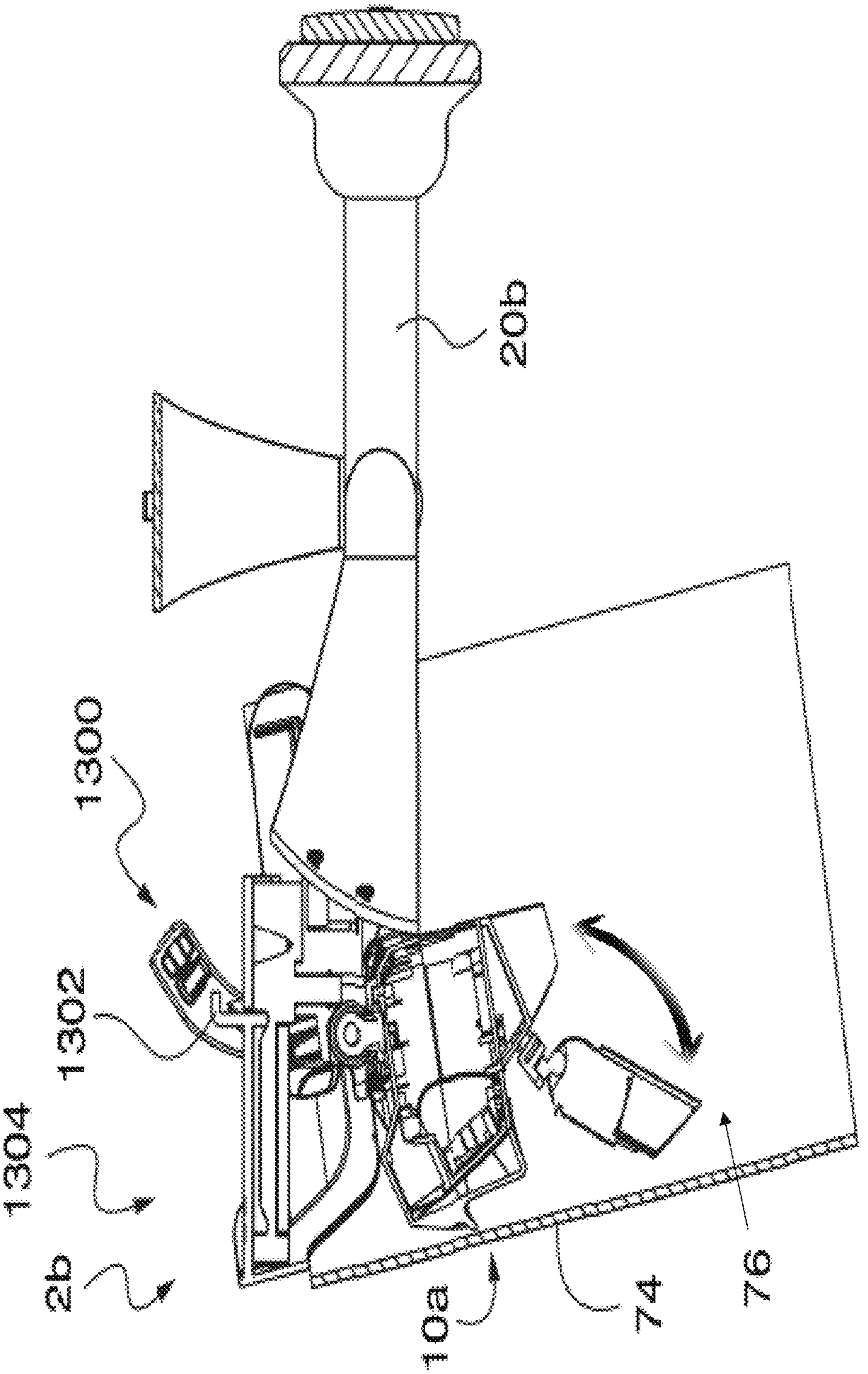
FIG. 5 is a schematic, side, cut-away view of the face shield being attached to the PPE adapter system for use with the first AR device with the AR device being rotated down, constructed according to an embodiment of the present invention.
Figure 6:
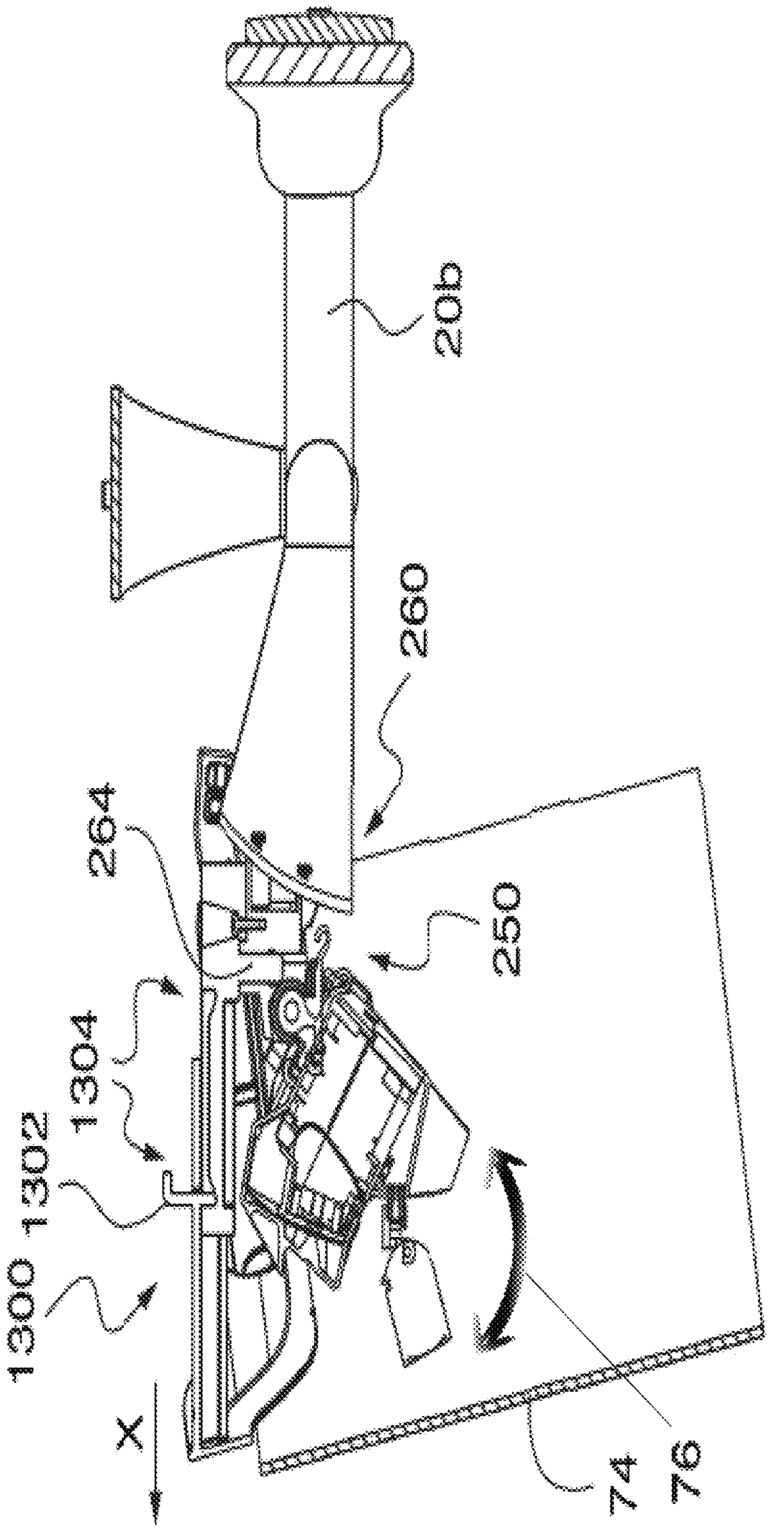
FIG. 6 is a schematic, side, cut-away view of the face shield being attached to the PPE adapter system for use with the first AR device with the AR device being rotated up, constructed according to an embodiment of the present invention.

With respect to FIGS. 2, 4 and 6, there are illustrated sliding adapter carrier 260. In particular, sliding adapter carrier 260 includes, in part, extension 264. In one embodiment, sliding adapter carrier 260 is constructed so that extension 264 will be placed (located) within an opening in extension 255 of sliding adapter mount 250. The sliding adapter carrier 260 will then be removable attached to a sliding adapter 1300 (FIGS. 3-6), as will be discussed in greater detail later. Preferably, sliding adapter carrier 260 is constructed of any suitable durable, UV resistant, heat resistant, lightweight, high strength polymeric material.

With respect to FIGS. 3-6, there is illustrated PPE adapter system 50*b* being attached to AR device 2*b*. As shown in FIGS. 3-6, PPE adapter system 50*b* includes, in part, wall 54*b*, hook and loop fasteners 72*b*, and sliding adapter 1300. It is to be understood that wall 54*b* and hook and loop fasteners 72*b* are constructed using conventional techniques such as printing, forming, molding or the like. Preferably, PPE adapter system 50*b* is constructed of any suitable durable, UV resistant, heat resistant, lightweight, high strength polymeric material.

With respect to FIGS. 2-6, there is illustrated PPE adapter system 50*b* being removably attached to AR device 2*b* through the use of sliding adapter 1300. In particular, PPE adapter system 50*b* is located on AR device 2*b* so that sliding adapter 1300 can be used to rotate AR device 2*b* towards and away from face shield 74.

A unique aspect of the present invention is the use of sliding adapter 1300. As shown in FIGS. 2-6, sliding adapter 1300 includes, in part, sliding adapter lever holder 1301, release lever 1302, a plurality of lever stops 1304, sliding adapter mount 250, and sliding adapter carrier 260. As discussed above, sliding adapter mount 250 is attached to AR device 2*b* through the use of a conventional fastener (not shown). The extension 264 is located within an opening 266 in extension 255. The extension 255 is then removably attached to head band 20*b*.

A unique aspect of the present invention is the ability of the PPE adapter system 50*b* to be able to attach to a face shield 74 (FIGS. 3-6) and allow the AR device 2*b* to be rotated towards face shield 74. In particular, as shown in FIGS. 3-6, a conventional face shield 74 can be attached to the PPE adapter system 50*b*. As discussed above, it is important to understand that in many medical procedures such as surgical procedures, a face shield 74 may be required to be worn by the medical personnel performing the surgical procedure. However, the present invention allows the AR device 2*b* to be tilted at an angle 76 with respect to the face shield 74. In this manner, PPE adapter system 50*b* is designed to rotate the AR device 2*b* in order to move the AR device 2*b* as close to the face shield 74, as possible. This is needed so the front camera 10*a* can calculate depth of objects without producing additional artifacts such as reflections. Furthermore, the tilt angle of face shield 74 with respect to front camera 10*a* should range between 5 and 15° with the preferable tilt angle being 10° in order to allow the face shield 74 to be in close proximity to the front camera 10*a*.

Figure 8:
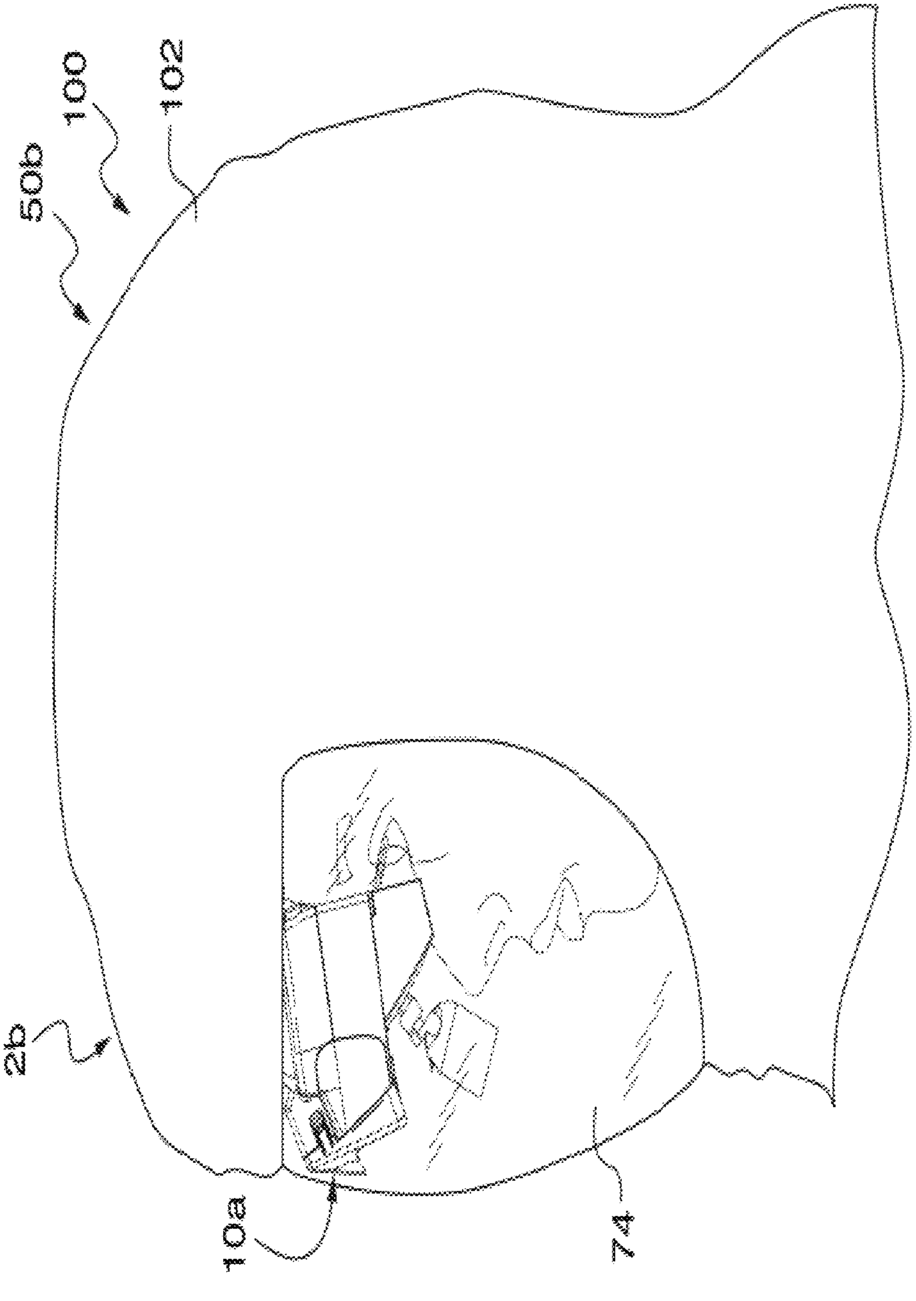
FIG. 8 is a side view of the PPE adapter system being attached to the first AR device and the PPE adapter system being worn by a user while the user is donning a PPE having a hood, constructed according to an embodiment of the present invention.

Another unique aspect of the present invention is the use of sliding adapter 1300. In particular, as shown in FIGS. 3-6, the AR device 2*b* is rotated down for viewing and the sliding adapter 1300 is slid back towards the head band 20*b* so that the face shield 74 is located in close proximity to the front camera 10*a* (FIG. 5). In order to rotate the AR device 2*b* upwardly, as shown in FIG. 6, the release lever 1302 is lifted up and away from the plurality of stops 1304 and moved in the direction of arrow X. The release lever 1302 is then located within one of the desired plurality of stops 1304. The release lever 1302 allows the sliding adapter 1300 to move forward which then creates the clearance needed for the AR device 2*b* to be rotated upwardly and away from the user's face in order to allow the medical personnel to view the surgical field without the AR device 2*b* being in the visual field of the medical personnel (FIG. 8). Preferably, the total travel length of the release lever 1302 is approximately 50 mm.

Figure 13:
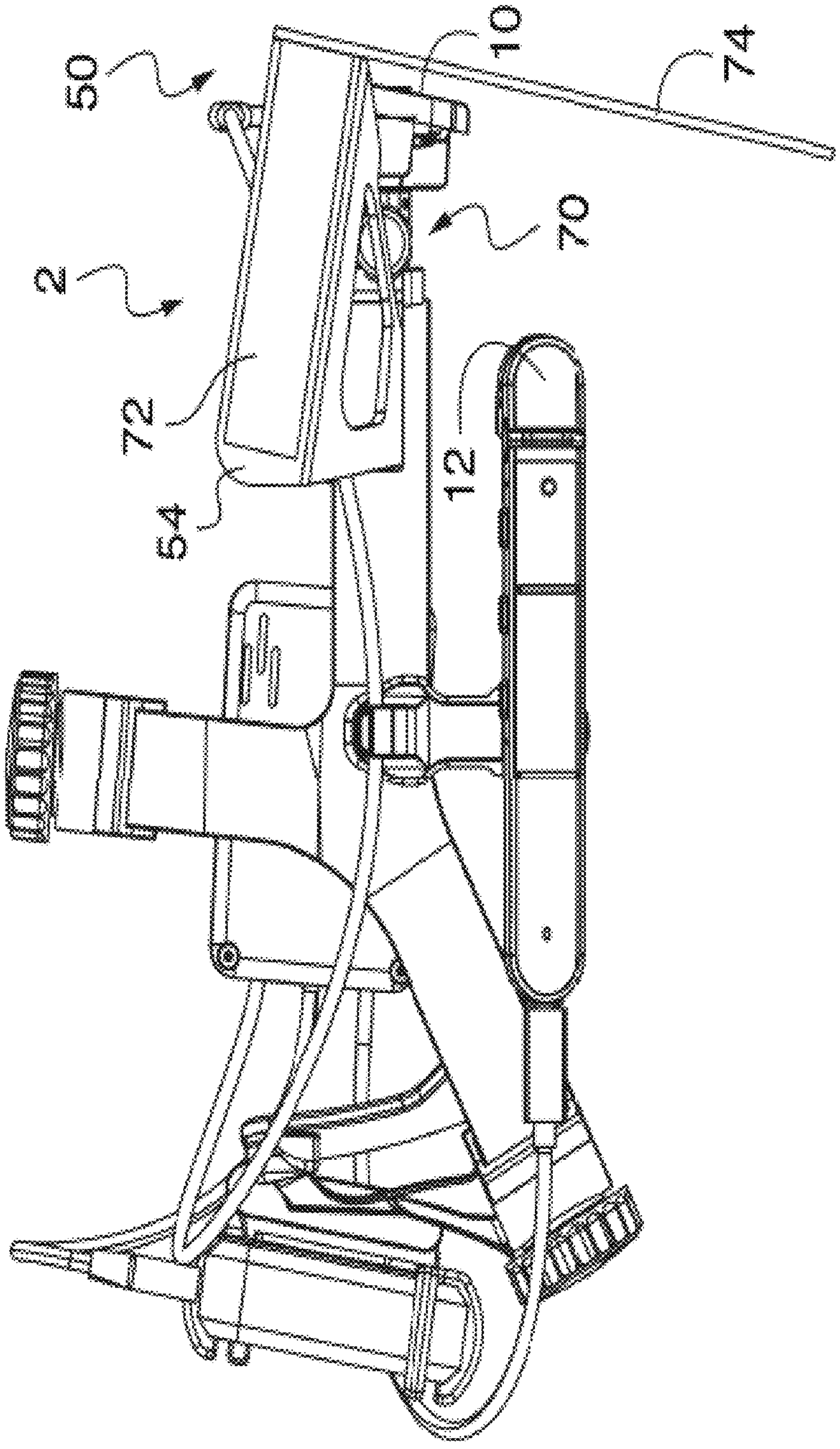
FIG. 13 is a schematic, side view of the face shield being attached to the PPE adapter system for use with the second AR device, constructed according to an embodiment of the present invention.
Figure 14:
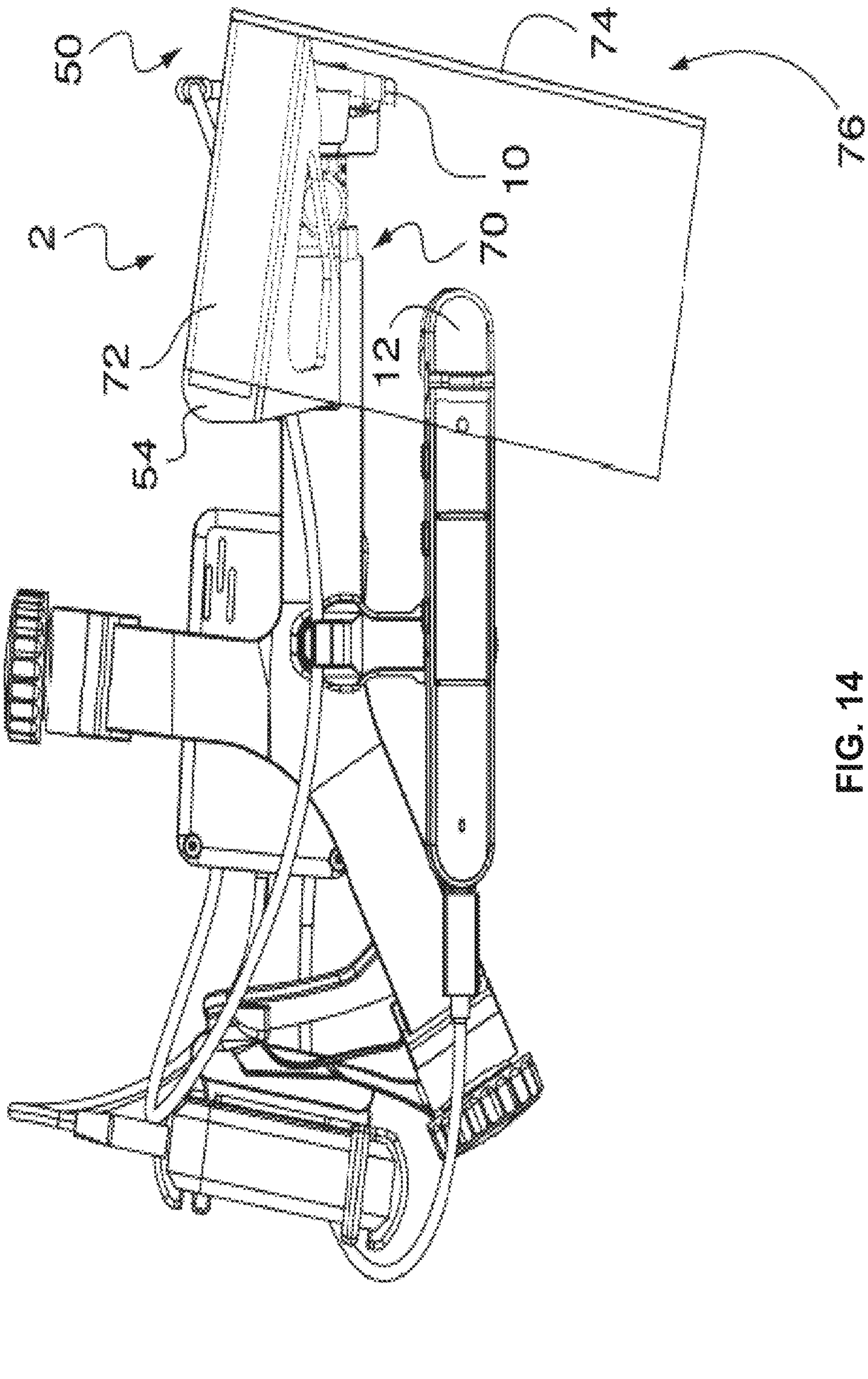
FIG. 14 is another schematic, side view of the face shield being attached to the PPE adapter system for use with the second AR device, constructed according to an embodiment of the present invention.

A still another unique aspect of the present invention is the use of hook and loop fasteners 72*b* located around a periphery of wall 54*b*. Preferably, hook and loop fasteners 72*b* are constructed in a similar manner as hook and loop fasteners 72 (FIGS. 13 and 14). The unique aspect of use of the hook and loop fasteners 72*b* is that the hook and loop fasteners 72*b* allow the PPE adapter system 50*b* to be removably attached to the face shield 74 (FIG. 3). In this manner, once the PPE adapter system 50*b* has been removably attached to AR device 2*b* and the AR device 2*b* has been placed on the head of the medical personnel, the surgical gown 100 can be located over the medical personnel and the hood 102 can be securely attached to the PPE adapter system 50*b* so that the face shield 74 and hood 102 remain in place on the medical personnel, especially during the medical procedure. As shown in FIG. 3, the hook and loop fasteners 72*b* can be attached to the hood at a location along a top edge of the face shield 74.

Figure 7:
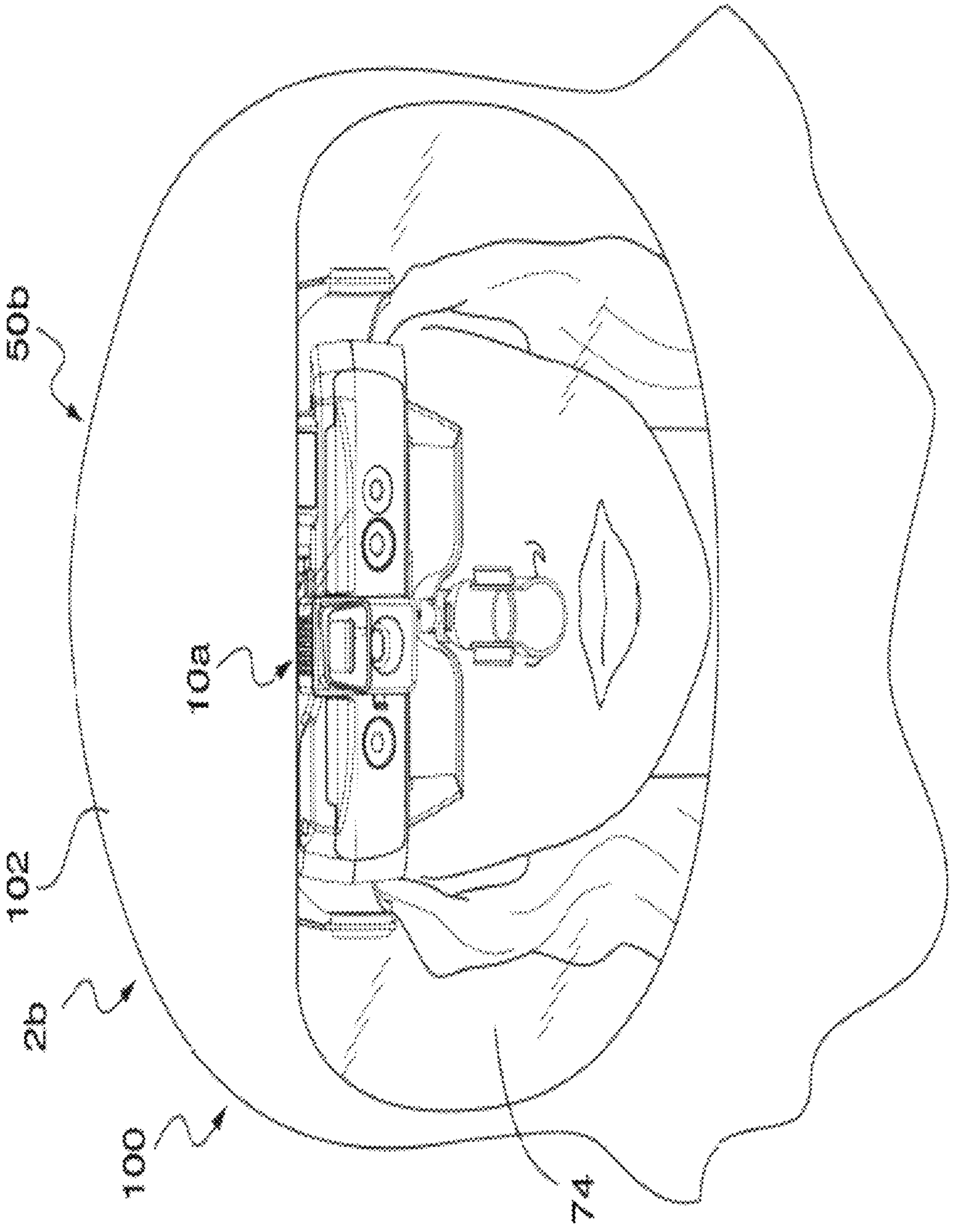
FIG. 7 is a front view of the PPE adapter system being attached to the first AR device and the PPE adapter system being worn by a user while the user is donning a PPE having a hood, constructed according to an embodiment of the present invention.

Furthermore, with respect to FIGS. 7 and 8, there are illustrated several different views of the PPE adapter system 50*b* being attached to the AR device 2*b* and the AR device 2*b* being worn by a user such as medical personnel. As shown in FIGS. 7 and 8, the PPE adapter system 50*b* has been attached to the AR device 2*b* and the AR device 2*b* is being worn by a user such as medical personnel. As shown in FIGS. 7 and 8, the medical personnel has donned a surgical gown 100 having a hood 102 and a face shield 74. As best shown in FIG. 8, the face shield 74 is located in close proximity to the front camera 10*a* so that the face shield 74 does not produce additional artifacts such as reflections when the front camera 10*a* is being utilized. As shown in FIG. 8, the AR device 2*b* has been rotated up so that the medical personnel can see the visual field without having to look through the AR device 2*b*.

PPE Adapter System for Use with a Second AR Device

Figure 9:
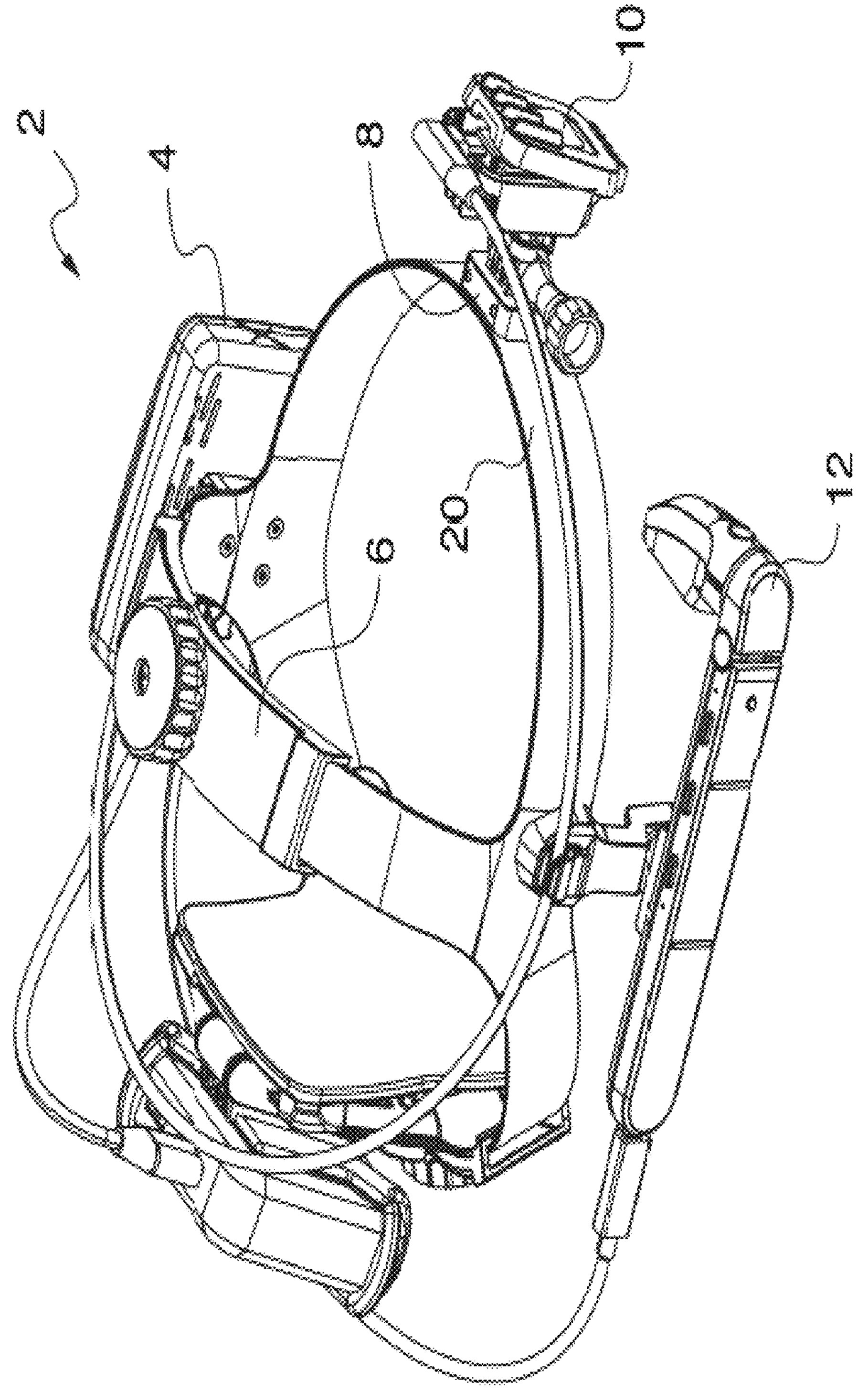
FIG. 9 (Prior Art)
FIG. 9 is a schematic, isometric view of one embodiment of a second AR device, according to the prior art.
Figure 10:
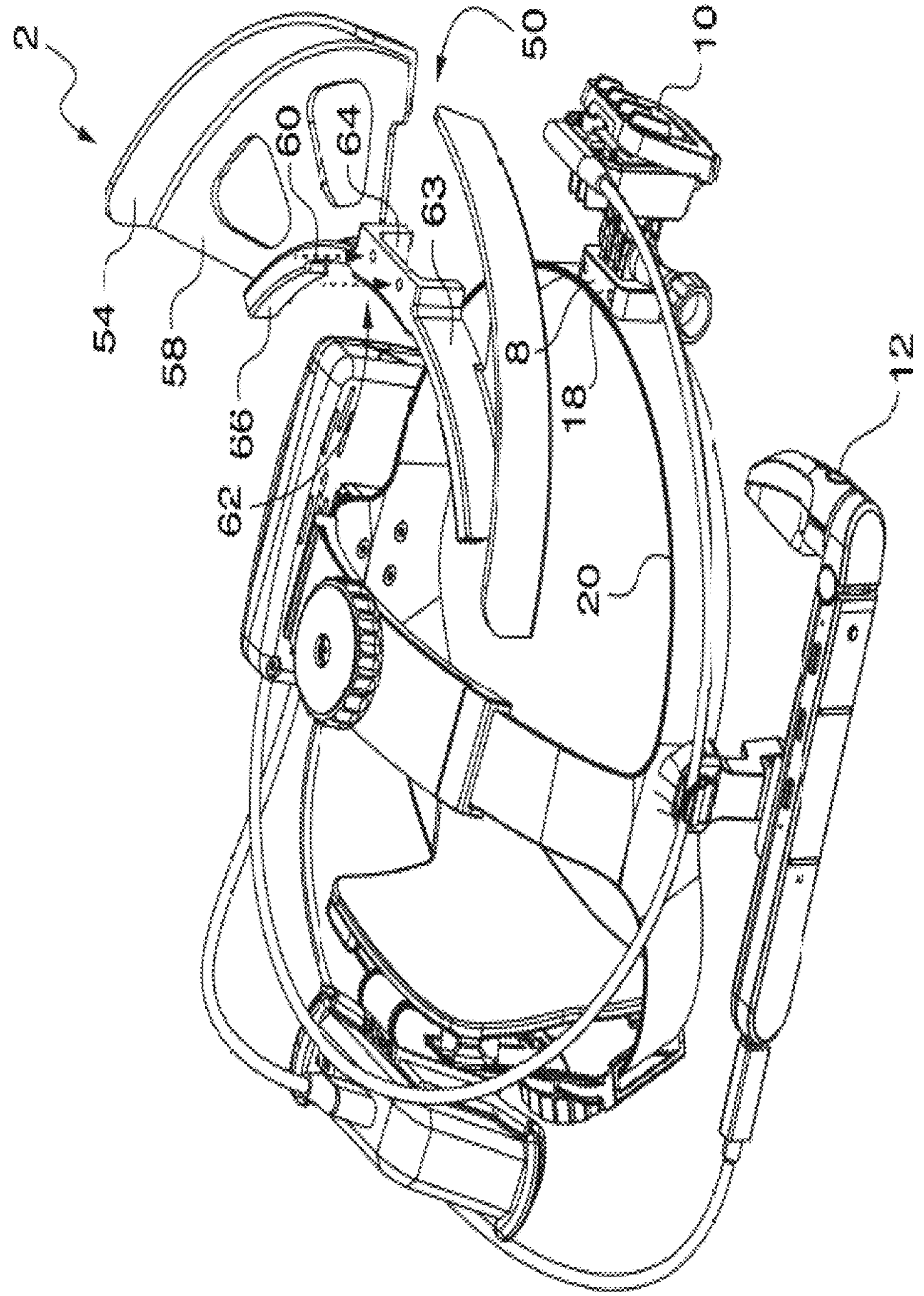
FIG. 10 is a top, isometric view of the PPE adapter system prior to being attached to the second AR device, constructed according to an embodiment of the present invention.

Referring now to FIG. 9-18, there is illustrated a personal protective equipment ("PPE") adapter system 50 for use with another augmented reality ("AR") device 2. As shown in FIGS. 9 and 10, there is illustrated one embodiment of a conventional AR device 2. Typically, AR device 2 includes, in part, a computer module 4, head gear 6, a mount 8 for assisting in mounting the front camera 10 and the PPE adapter system 50, and AR viewing display 12, threaded openings 18, and headband 20. It is to be understood that the mount 8 is located adjacent to the front camera 10.

Figure 11A:
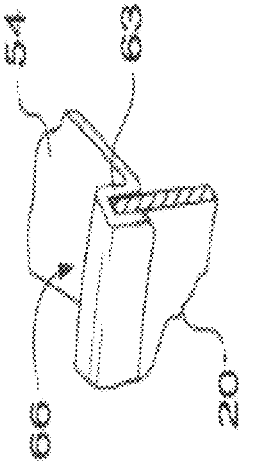
FIG. 11A is a schematic, close-up view of the PPE adapter system prior to being attached to the second AR device, constructed according to an embodiment of the present invention.
Figure 11:
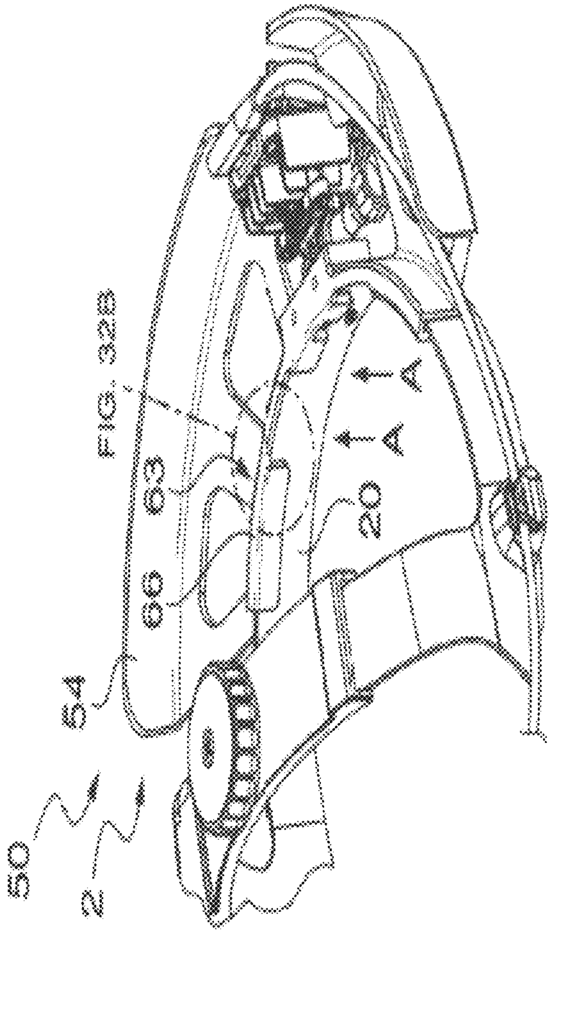
FIG. 11 is a schematic, top view of the PPE adapter system being attached to the second AR device, constructed according to an embodiment of the present invention.
Figure 12:
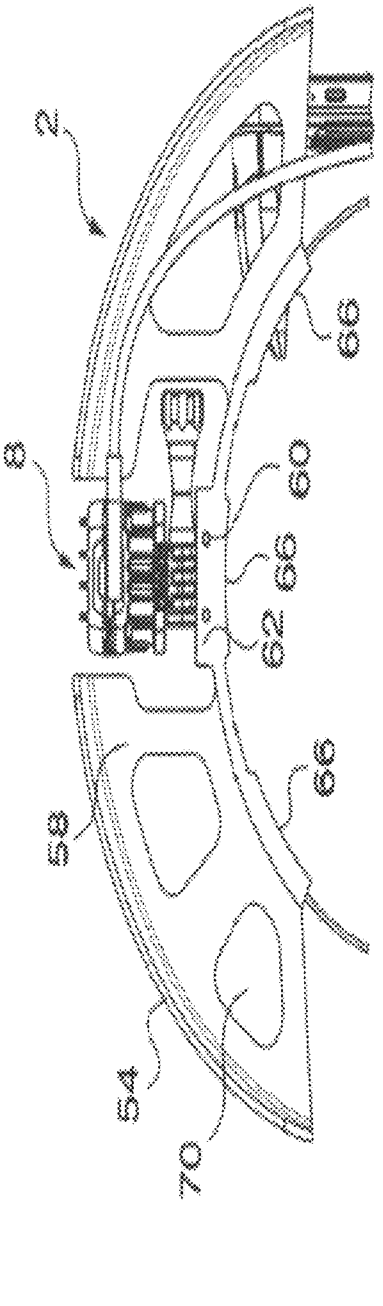
FIG. 12 is a top view of the PPE adapter system being attached to the second AR device, constructed according to an embodiment of the present invention.

With respect to FIGS. 10-12, there are illustrated PPE adapter system 50 prior to being attached to AR device 2. As shown in FIGS. 10-12, PPE adapter system 50 includes, in part, wall 54, extension 58, threaded fasteners 60, bracket 62, wall 63, bracket opening 64 (FIG. 10), and channels 66. Preferably, except for threaded fasteners 60, PPE adapter system 50 is constructed of any suitable durable, UV resistant, heat resistant, lightweight, high strength polymeric material.

With respect to FIGS. 11, 11A, and 12, there is illustrated PPE adapter system 50 being removably attached to AR device 2. In particular, PPE adapter system 50 is located on AR device 2 so that channels 66 are retained along portions of headband 20. Also, bracket 62 is removably retained on mount 8 through the use of threaded fasteners 60 and threaded fastener openings 18 (FIG. 10).

A unique aspect of the present invention is the use of openings 70 (FIG. 11) in PPE adapter system 50. In particular, openings 70 are open areas on the PPE adapter system 50 that allow for air to circulate within a hood 100 (FIGS. 16 and 18), reduce weight, and reduce material usage in constructing the PPE adapter system 50.

Another unique aspect of the present invention is that the PPE adapter system 50 can be easily and quickly attached to the AR device 2 and removed from the AR device 2. In particular, bracket 62 can be quickly located over mount 8. The channels 66 can also be located over headband 20. The PPE adapter system 50 can then be removably attached to the AR device 2 through the use of the threaded fasteners 60 and threaded fastener openings 18. The PPE adapter system 50 can be securely attached to the AR device 2 by placing the channels 66 over the headband 20 and attaching the threaded fasteners 60 to the threaded fastener openings 18. Conversely, the PPE adapter system 50 can be easily and quickly removed from the AR device 2 by removing the threaded fasteners 60 from the threaded fastener openings 18 and lifting the channels 66 off of the headband 20 in the direction of arrows A (FIG. 11).

A yet another unique aspect of the present invention is the ability of the PPE adapter system 50 to be able to attach to a face shield 74 (FIGS. 13 and 14). In particular, as shown in FIGS. 13 and 14, a conventional face shield 74 can be attached to the PPE adapter system 50. It is important to understand that in many medical procedures such as surgical procedures, a face shield 74 may be required to be worn by the medical personnel performing the surgical procedure. However, the present invention allows the face shield 74 to be tilted at an angle 76 with respect to the front camera 10 of the AR device 2. In this manner, PPE adapter system 50 is designed to have a forward tilt in order to move the face shield 74 as close to the front camera 10, as possible. This is needed so the front camera 10 can calculate depth of objects without producing additional artifacts such as reflections. Furthermore, the tilt angle 76 should range between 5 and 15° with the preferable tilt angle being 10° in order to allow the face shield 74 to be in close proximity to the front camera 10.

A still another unique aspect of the present invention is the use of hook and loop fasteners 72 located around a periphery of wall 54 (FIGS. 13 and 14). Preferably, hook and loop fasteners 72 are constructed of Velcro® or any other similar hook and loop material. The unique aspect of use of the hook and loop fasteners 72 is that the hook and loop fasteners 72 allow the PPE adapter system 50 to be removably attached to the face shield 74. In this manner, once the PPE adapter system 50 has been removably attached to AR device 2 and the AR device 2 has been placed on the head of the medical personnel, the surgical gown 100 (FIG. 16) can be located over the medical personnel and the hood 102 can be securely attached to the PPE adapter system 50 so that the face shield 74 and hood 102 remain in place on the medical personnel, especially during the medical procedure. As shown in FIGS. 13 and 14, the hook and loop fasteners 72 can be attached to the hood at a location along a top edge of the face shield 74.

Figure 15:
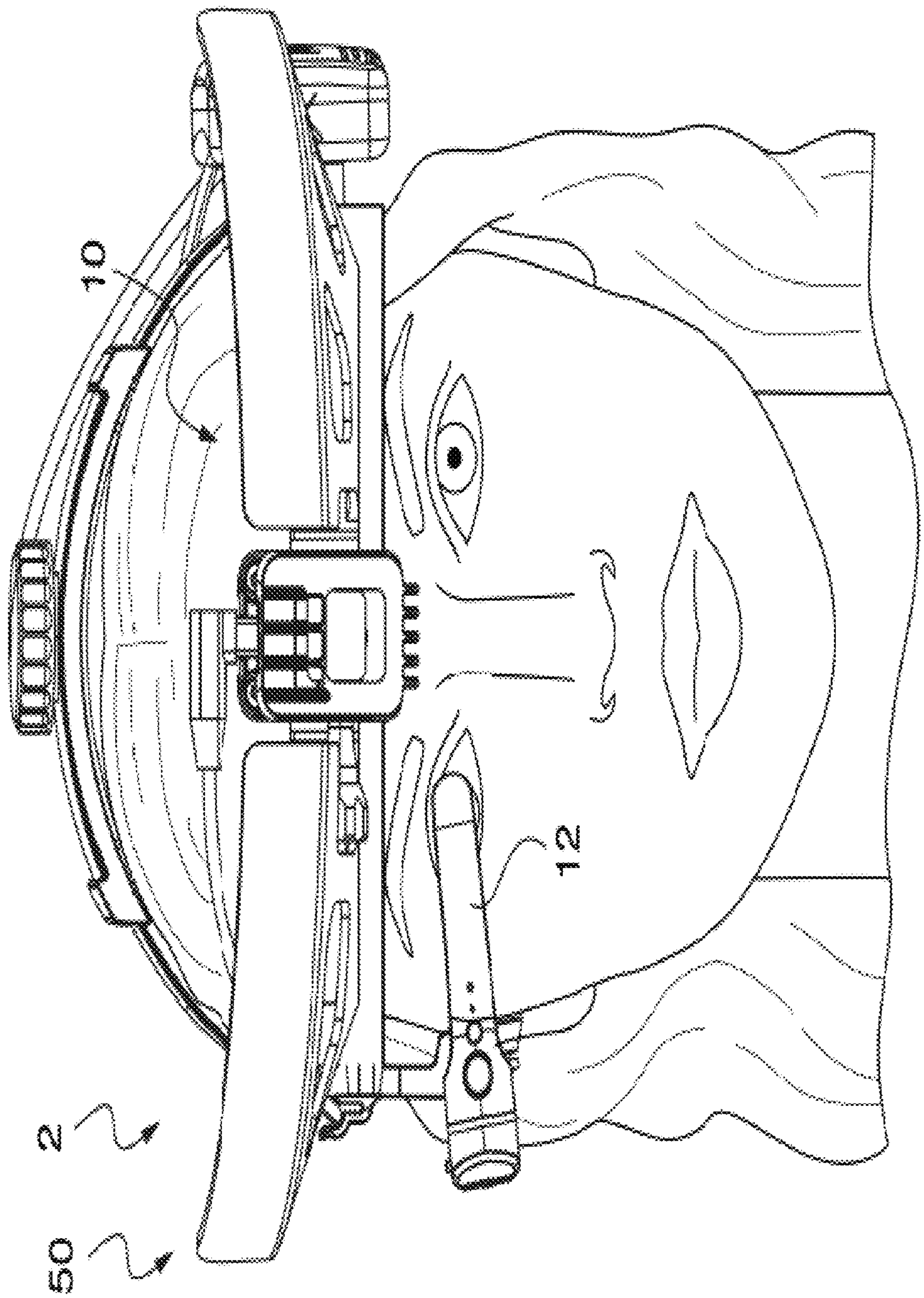
FIG. 15 is a front view of the PPE adapter system being attached to the second AR device and the PPE adapter system being worn by a user, constructed according to an embodiment of the present invention.
Figure 16:
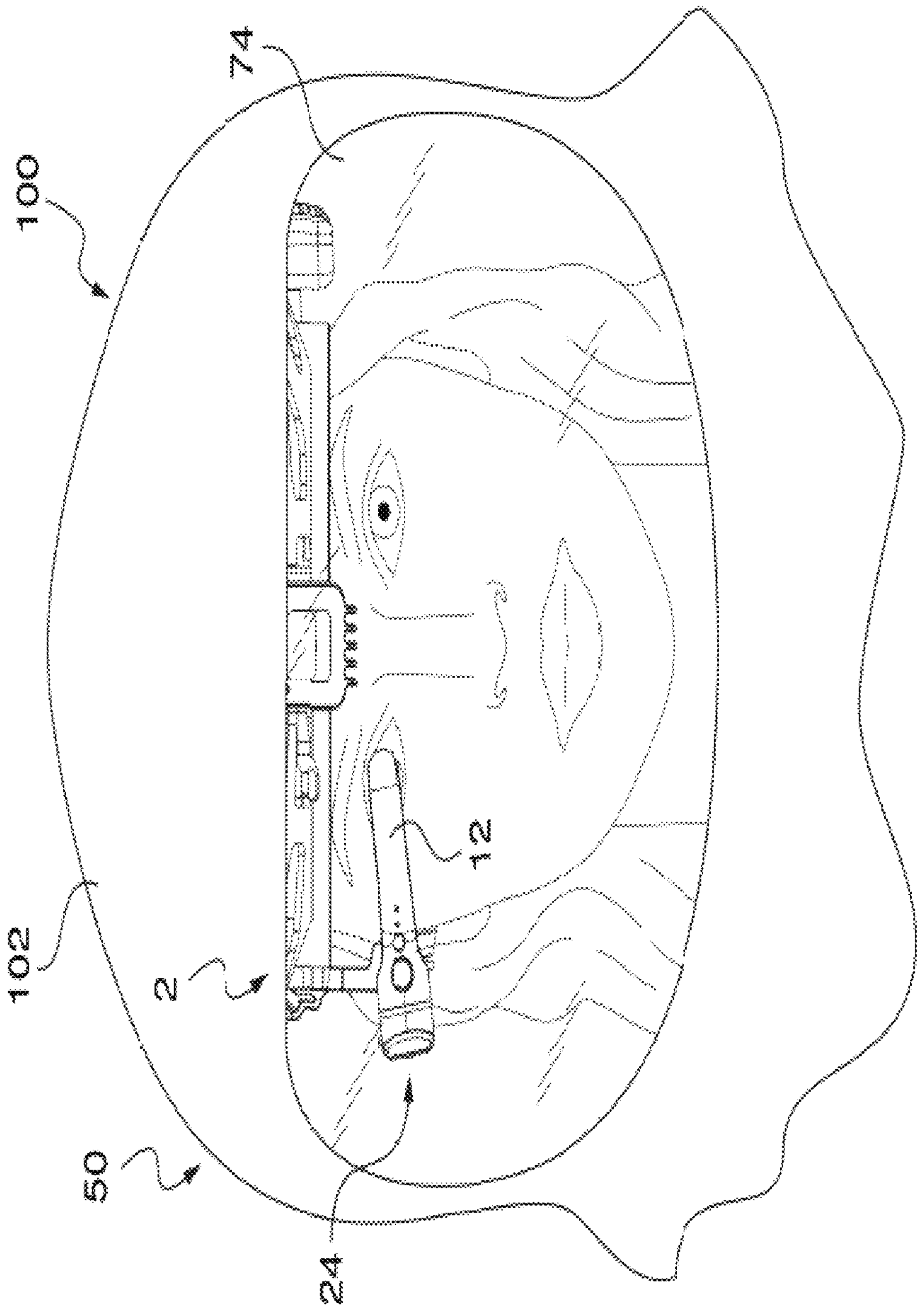
FIG. 16 is a front view of the PPE adapter system being attached to the second AR device and the PPE adapter system being worn by a user while the user is donning a PPE having a hood, constructed according to an embodiment of the present invention.
Figure 17:
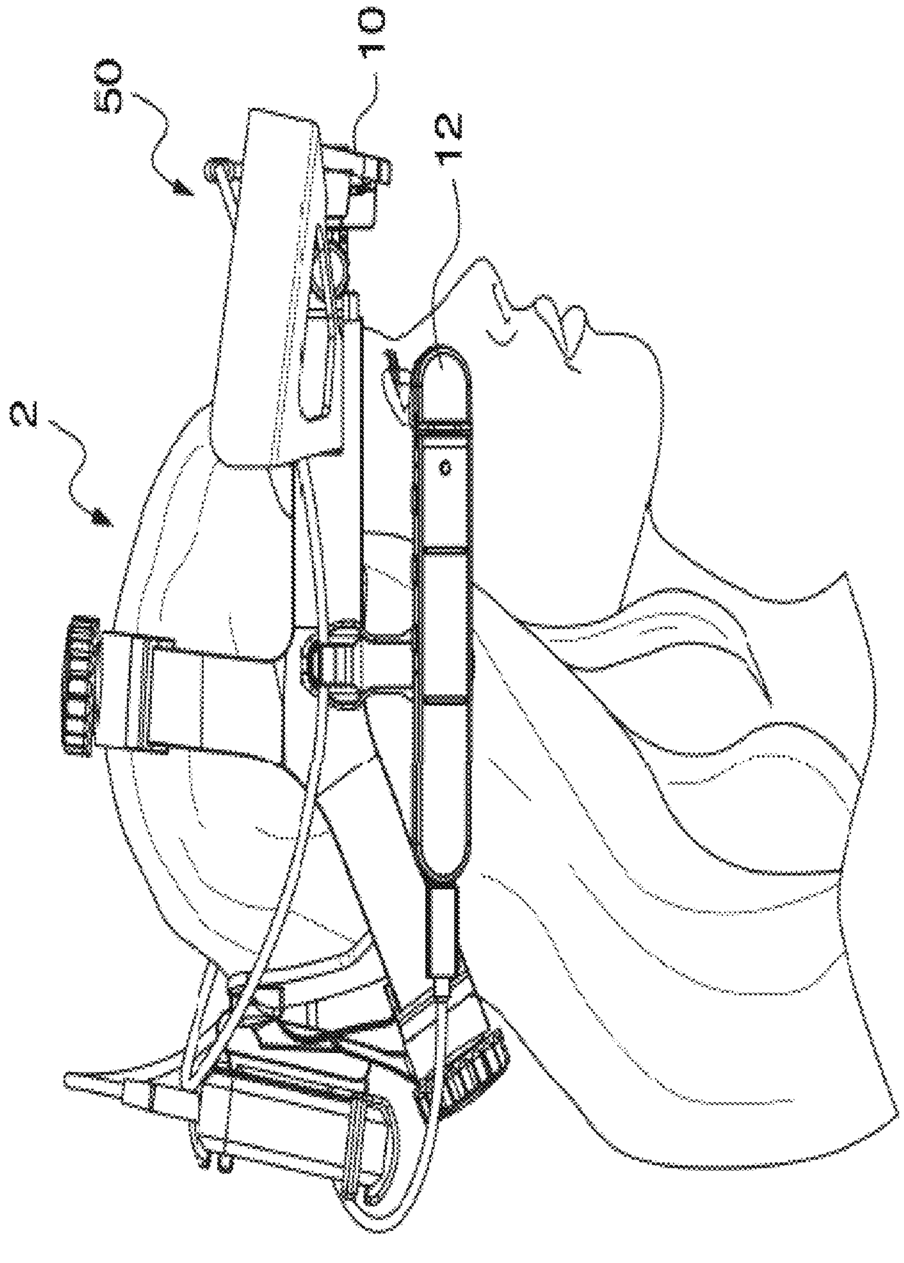
FIG. 17 is a side view of the PPE adapter system being attached to the second AR device and the PPE adapter system being worn by a user, constructed according to an embodiment of the present invention.
Figure 18:
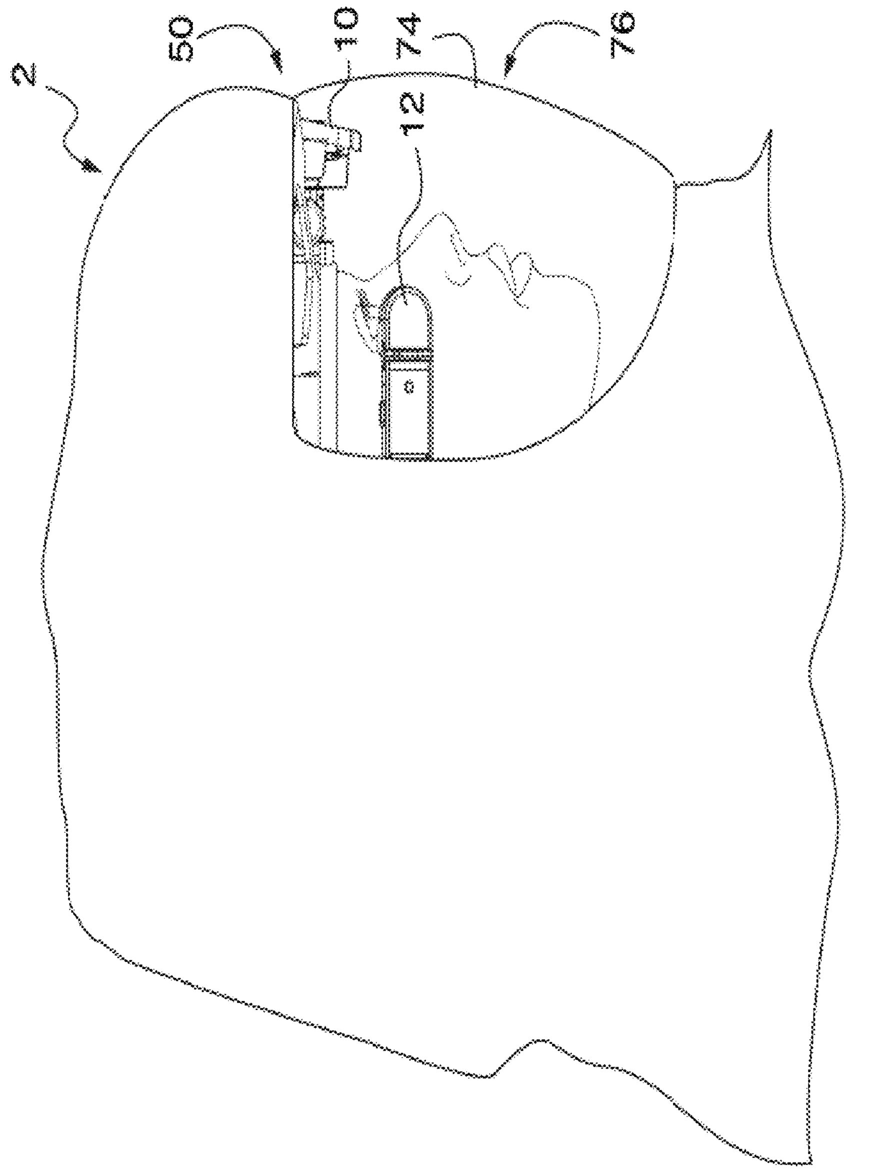
FIG. 18 is a side view of the PPE adapter system being attached to the second AR device and the PPE adapter system being worn by a user while the user is donning a PPE having a hood, constructed according to an embodiment of the present invention.

With respect to FIGS. 15-18, there are illustrated several different views of the PPE adapter system 50 being attached to the AR device 2 and the AR device 2 is being worn by a user such as medical personnel. As shown in FIGS. 15 and 17, the PPE adapter system 50 has been attached to the AR device 2 and the AR device 2 is being worn by a user such as medical personnel. As shown in FIGS. 16 and 18, the medical personnel has donned a surgical gown 100 having a hood 102 and a face shield 74. As best shown in FIG. 18, the face shield 74 is located in close proximity to the front camera 10 of the AR device 2 so that the face shield 74 does not produce additional artifacts such as reflections when the front camera 10 is being utilized.

PPE Adapter System for Use with a Third AR Device

Figure 19:
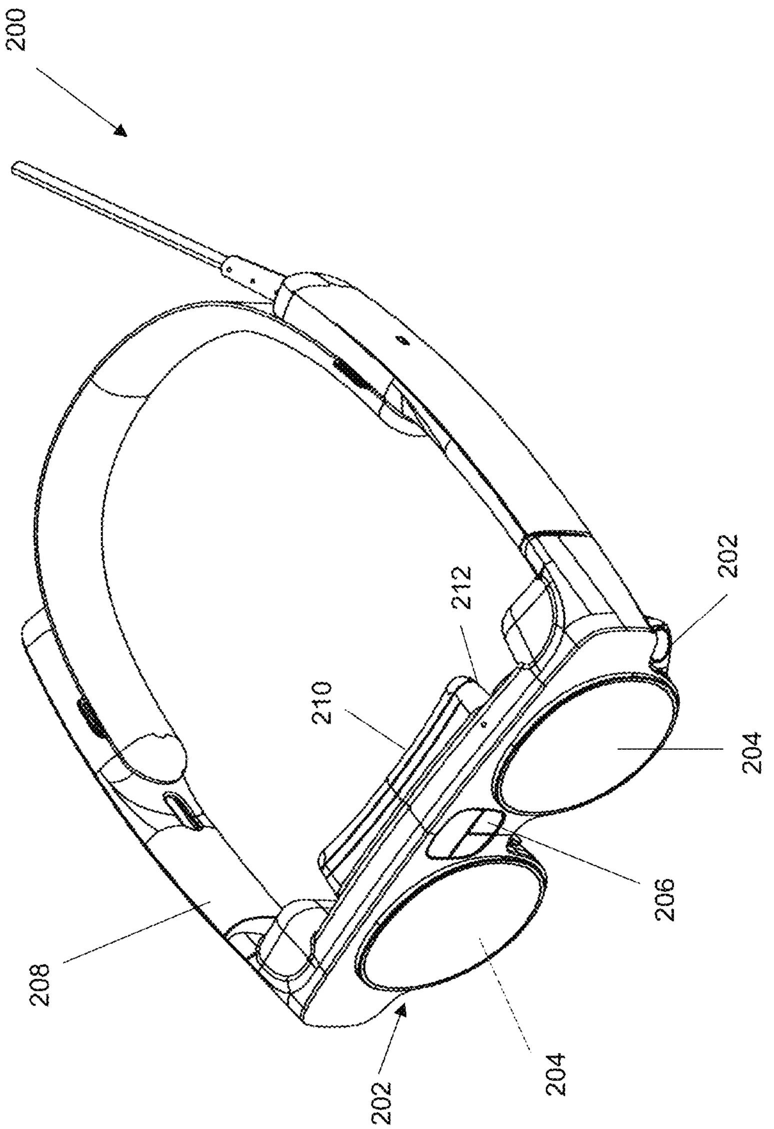
FIG. 19 (Prior Art)
FIG. 19 is a schematic, isometric view of one embodiment of a third AR device, according to the prior art.

Referring now to FIG. 19-27, there is illustrated a personal protective equipment ("PPE") adapter system 350 for use with another augmented reality ("AR") device 200. As shown in FIG. 19, there is illustrated one embodiment of a conventional AR device 200. Typically, AR device 200 includes, in part, side sensor arrays 202, direct view, transparent, liquid crystal displays 204, center sensor array 206, head band 208, and head piece 210. It is to be understood that there are two (2) side sensor arrays 202 with each being located next to one of the direct view, transparent, liquid crystal displays 204. Also, it is to be understood that there are two (2) direct view, transparent, liquid crystal displays 204.

Figure 21:
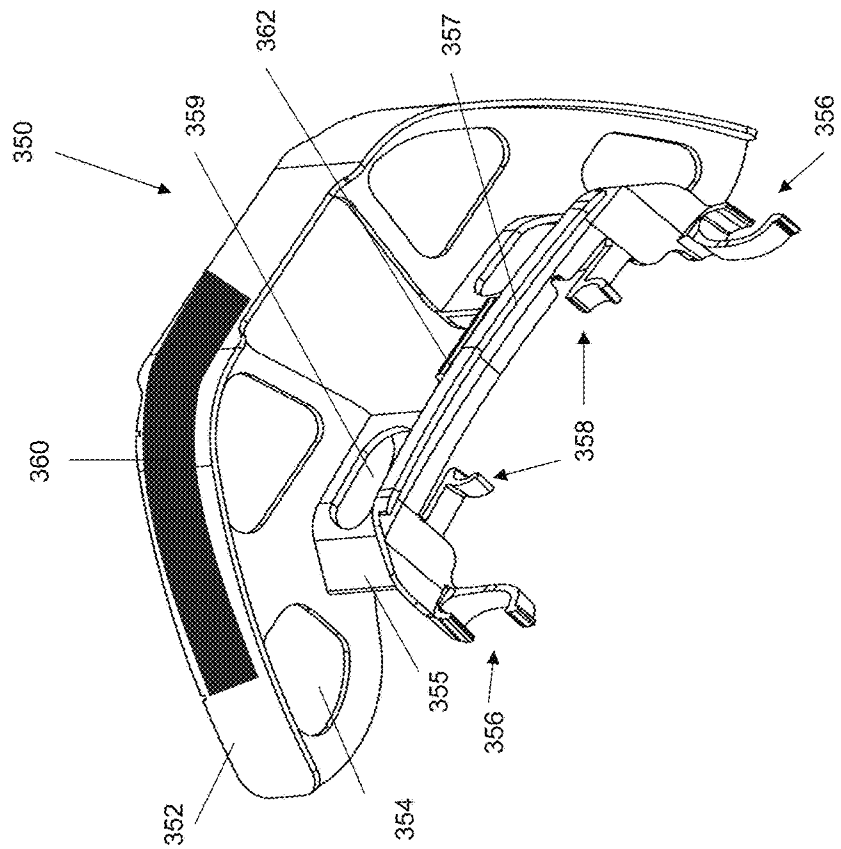
FIG. 21 is a bottom, isometric view of the PPE adapter system prior to being attached to the third AR device, constructed according to an embodiment of the present invention.
Figure 20:
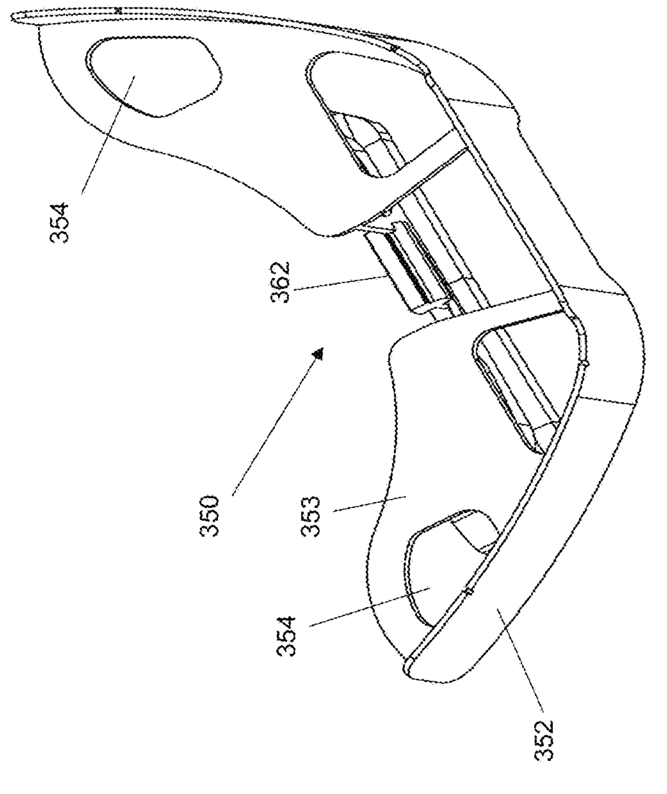
FIG. 20 is a top, isometric view of the PPE adapter system prior to being attached to the third AR device, constructed according to an embodiment of the present invention.

With respect to FIGS. 20 and 21, there are illustrated PPE adapter system 350 prior to being attached to AR device 200. As shown in FIGS. 20 and 21, PPE adapter system 350 includes, in part, wall 352, extension 353, extension openings 354, extensions 355, primary interface clips 356, bracket 357, secondary interface clips 358, openings 359, hook and loop fasteners 360, and surgical light mounting bar 362. Preferably, except for extension openings 354, openings 359, and hook and loop fasteners 360, PPE adapter system 350 is constructed of any suitable durable, UV resistant, heat resistant, lightweight, high strength polymeric material. It is to be understood that each of the primary interface clips 356 is connected to one of the extensions 355 and each of the plurality of secondary interface clips 358 is connected to one of the plurality of primary interface clips 356.

Figure 22:
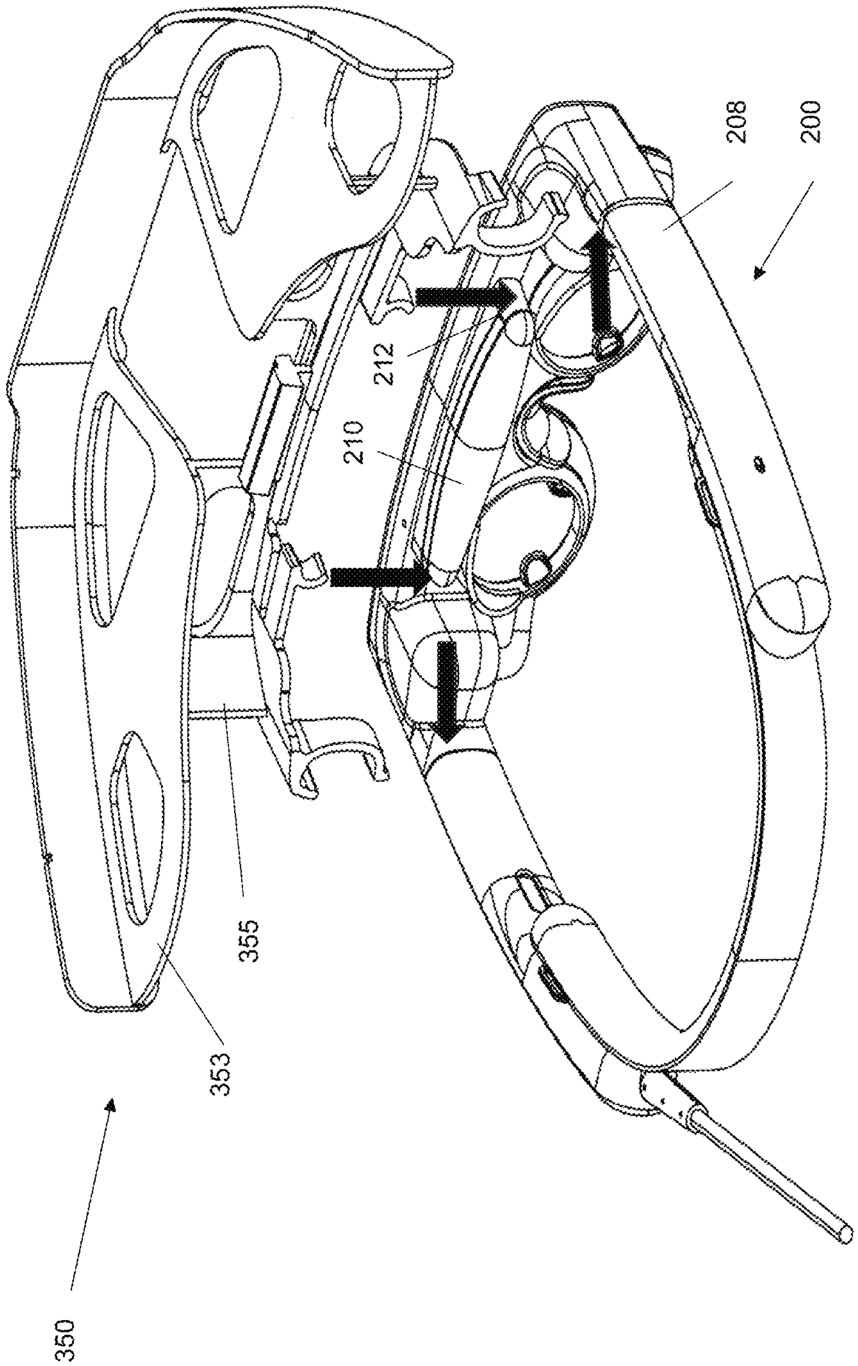
FIG. 22 is another schematic, top view of the PPE adapter system prior to being attached to the third AR device, constructed according to an embodiment of the present invention.

With respect to FIG. 22, there is illustrated PPE adapter system 350 being removably attached to AR device 200. In particular, PPE adapter system 350 is located on AR device 200 so that primary interface clips 356 are located over a portion of head band 208 adjacent to the direct view, transparent, liquid crystal displays 204. Also, secondary interface clips 358 are located over end portions 212 of head piece 210.

Figure 23:
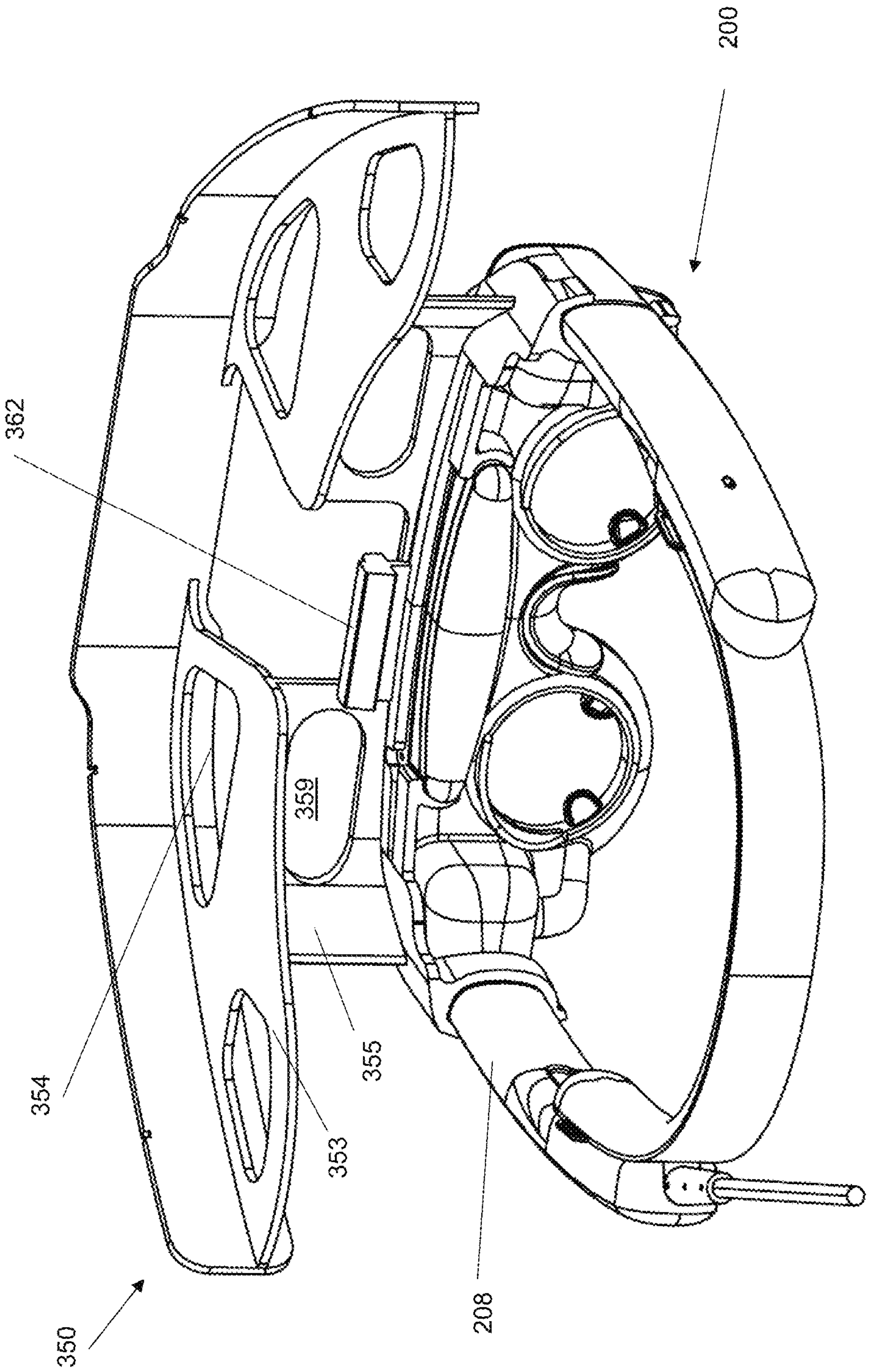
FIG. 23 is a schematic, top view of the PPE adapter system being attached to the third AR device, constructed according to an embodiment of the present invention.
Figure 24:
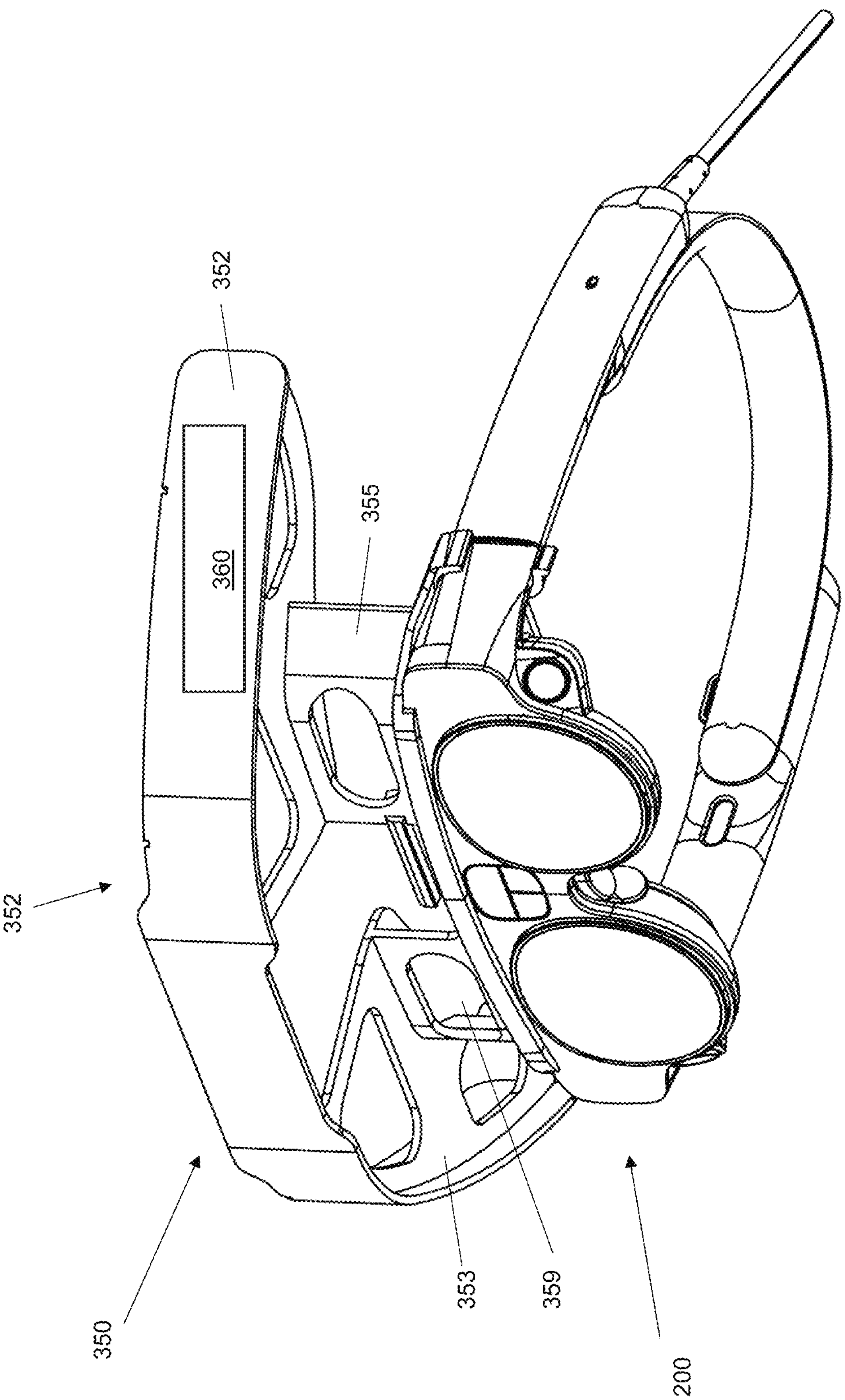
FIG. 24 is a schematic, front view of the PPE adapter system being attached to the third AR device, constructed according to an embodiment of the present invention.

With respect to FIGS. 23 and 24, there is illustrated PPE adapter system 350 being removably attached to AR device 200. In particular, PPE adapter system 350 is located on AR device 200 so that primary interface clips 356 interacts with and locks onto a portion of head band 208 adjacent to the direct view, transparent, liquid crystal displays 204 and secondary interface clips 358 interacts with and locks onto end portions of head piece 210.

Another unique aspect of the present invention is that the PPE adapter system 350 can be easily and quickly attached to the AR device 200 and removed from the AR device 200. In particular, primary interface clips 356 can be located over a portion of head band 208 adjacent to the direct view, transparent, liquid crystal displays 204 and secondary interface clips 358 can be located over end portions of head piece 210. The PPE adapter system 350 can then be removably attached to the AR device 200 through the use of the primary interface clips 356 and the secondary interface clips 358. The PPE adapter system 350 can be securely attached to the AR device 200 by having the primary interface clips 356 interact with and lock onto a portion of head band 208 adjacent to the direct view, transparent, liquid crystal displays 204 and secondary interface clips 358 interact with and lock onto end portions of head piece 210. Conversely, the PPE adapter system 350 can be easily and quickly removed from the AR device 200 by removing the primary interface clips 356 from the portion of head band 208 adjacent to the direct view, transparent, liquid crystal displays 204 and removing the secondary interface clips 358 from the end portions of head piece 210.

A unique aspect of the present invention is the use of openings 354 and 359 in PPE adapter system 350. In particular, openings 354 and 359 are open areas on the PPE adapter system 350 that allow for air to circulate within a hood 100 (FIG. 27), reduce weight, and reduce material usage in constructing the PPE adapter system 350.

Another unique aspect of the present invention is the addition of surgical light mounting bar 362 (FIG. 23). In one embodiment, a conventional surgical light (not shown) can be attached to the surgical light mounting bar 362 if additional lighting is needed by the medical personnel wearing the PPE adapter system 350.

Furthermore, it is known that augmented reality headsets (i.e., AR device 200) operate in "open air". That means they have no barriers between the augmented reality headset device and the environment. With the addition of a face shield, the face shield adds a physical obstruction to the field of view of the sensors and cameras commonly found on augmented reality headsets which creates challenges for the camera and sensors to map the environment and proximity to external masses (such as hands). Also, the face shield is typically curved which introduces undesirable refractivity to the system. In-order for the augmented reality headsets to operate correctly, the refraction needs to be significantly reduced or eliminated.

Figure 25:
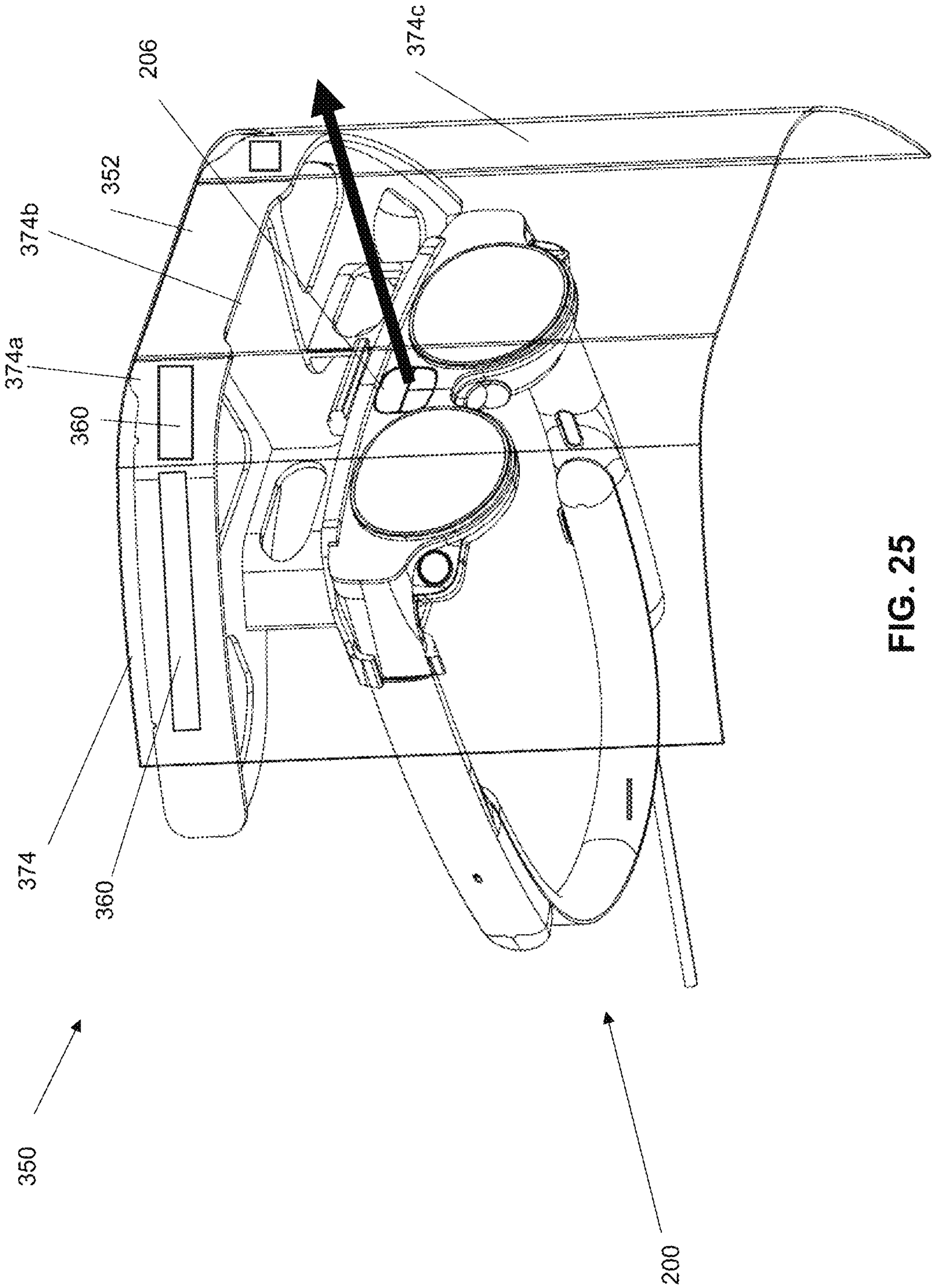
FIG. 25 is a schematic, bottom view of the face shield being attached to the PPE adapter system for use with the third AR device, constructed according to an embodiment of the present invention.

In order to address the refractivity issue, the face shield 374 of the present invention has been constructed to be as flat as possible and perpendicular to the center sensor array 206 as shown in FIG. 25.

Figure 26:
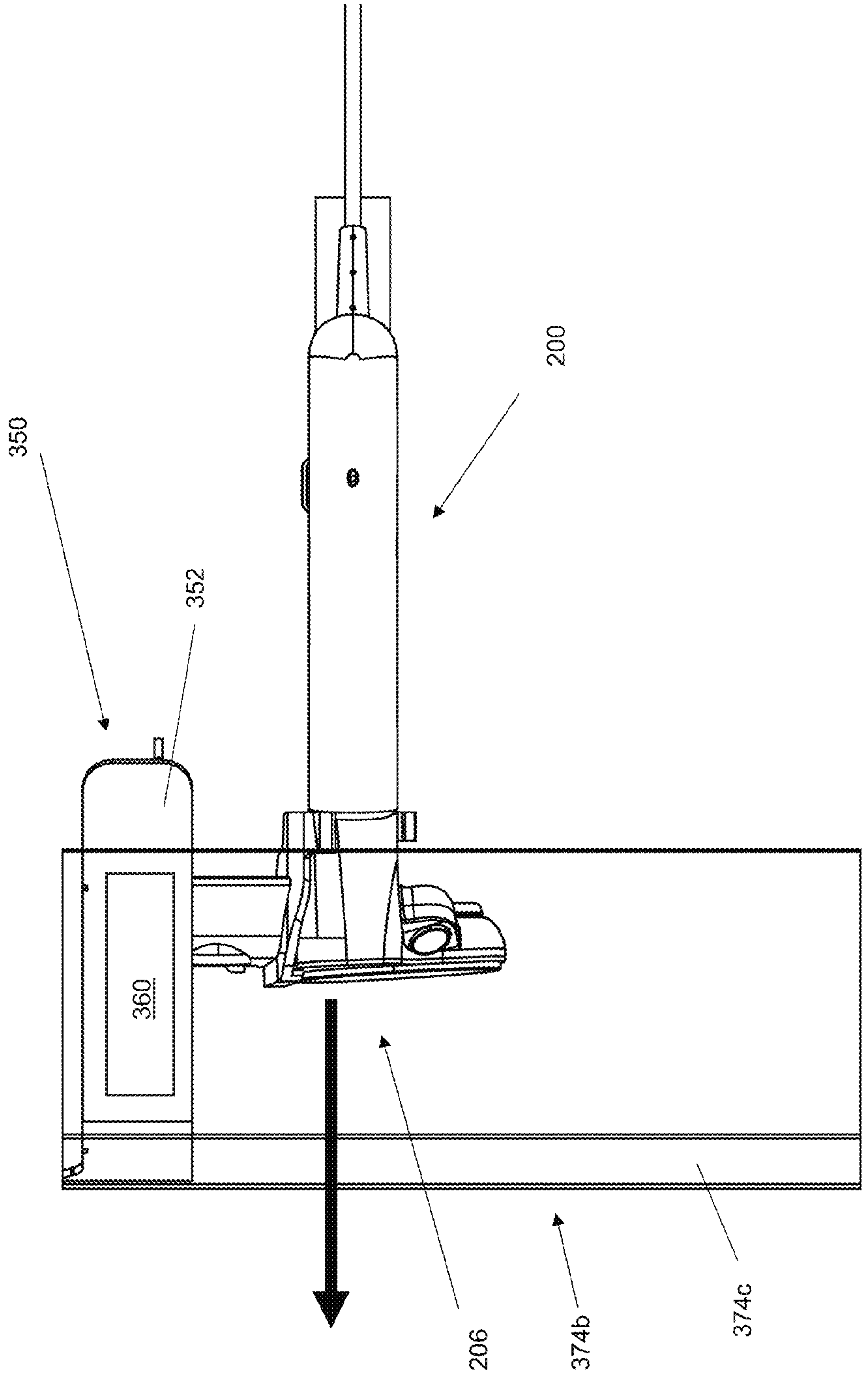
FIG. 26 is a schematic, side view of the face shield being attached to the PPE adapter system for use with the third AR device, constructed according to an embodiment of the present invention.

With respect to face shield 374, as shown in FIGS. 25 and 26, face shield 374 includes a curved portion 374*a*, a flat portion 374*b*, and a curved portion 374*c*. It is to be understood that the face shield 374 is constructed so that the flat portion 374*b* of the face shield 374 that is located directly in front of and in close proximity to center sensor array 206 (see arrow in FIG. 25). In this manner, since the viewing area directly in front of the center sensor array 206 is flat, the possibility of the center sensor array 206 experiencing any refractivity is significantly reduced or eliminated.

A yet another unique aspect of the present invention is the ability of the PPE adapter system 350 to be able to attach to a face shield 374 (FIGS. 21 and 24-26). In particular, as shown in FIGS. 25 and 26, a face shield 374 can be attached to the PPE adapter system 350. It is important to understand that in many medical procedures such as surgical procedures, a face shield 374 may be required to be worn by the medical personnel performing the surgical procedure. However, the present invention allows the face shield 374 to located perpendicular to the center sensor array 206 so that the possibility of the center sensor array 206 experiencing any refractivity is significantly reduced or eliminated.

A still another unique aspect of the present invention is the use of hook and loop fasteners 360 located around a periphery of wall 352 which are used to keep the face shield 374 located perpendicular with respect to the center sensor array 206 (FIGS. 21 and 24-26). Preferably, hook and loop fasteners 360 are constructed of Velcro® or any other similar hook and loop material. The unique aspect of use of the hook and loop fasteners 360 is that the hook and loop fasteners 360 allow the PPE adapter system 350 to be removably attached to the face shield 374. In this manner, once the PPE adapter system 350 has been removably attached to AR device 200 and the AR device 200 has been placed on the head of the medical personnel, the surgical gown 100 (FIG. 27) can be located over the medical personnel and the hood 102 can be securely attached to the PPE adapter system 350 so that the face shield 374 and hood 102 remain in place on the medical personnel, especially during the medical procedure.

Figure 27:
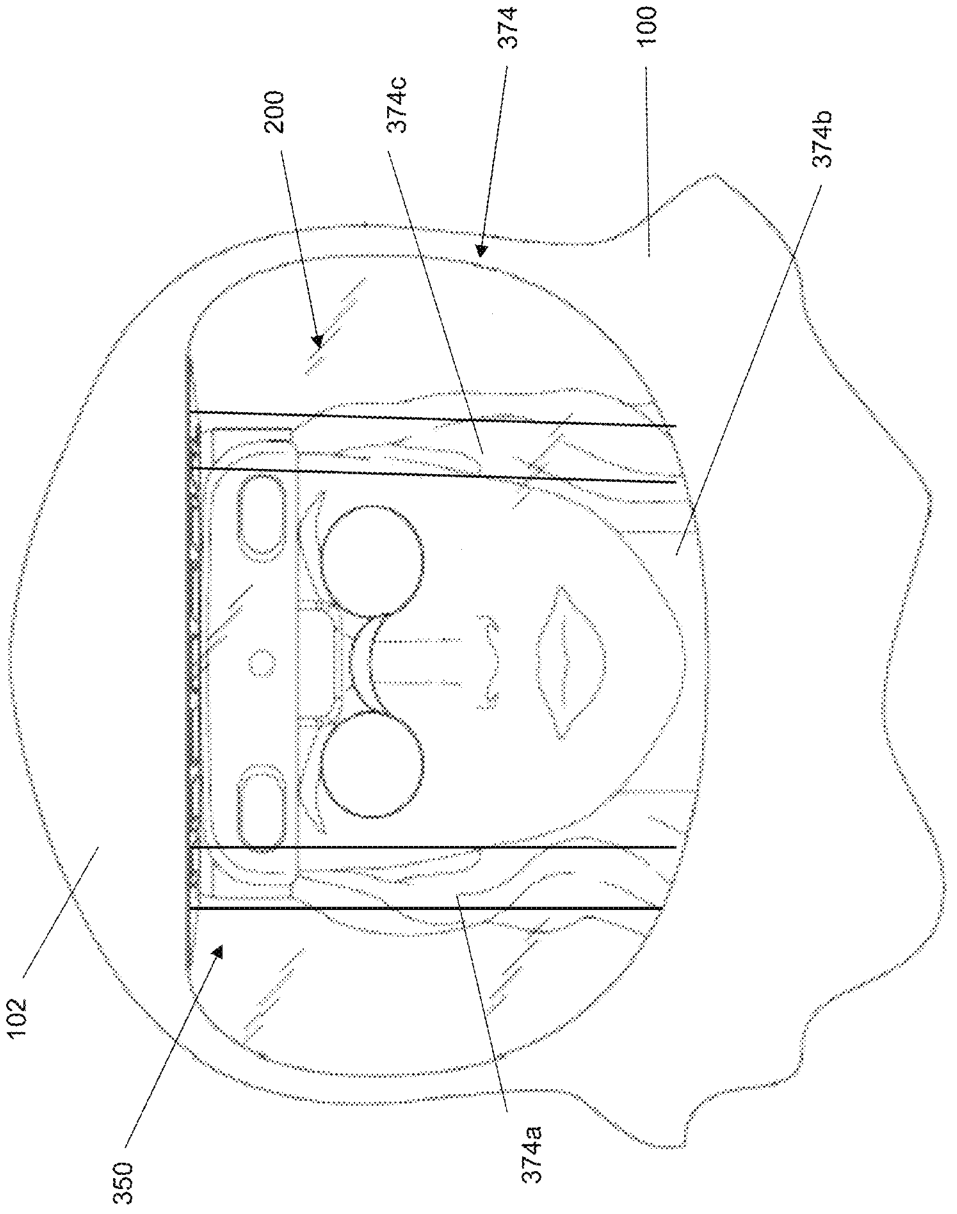
FIG. 27 is a front view of the PPE adapter system being attached to the third AR device and the PPE adapter system being worn by a user while the user is donning a PPE having a hood, constructed according to an embodiment of the present invention.

With respect to FIG. 27, there is illustrated a view of the PPE adapter system 350 being attached to the AR device 200 and the AR device 200 is being worn by a user such as medical personnel. As shown in FIG. 27, the PPE adapter system 350 has been attached to the AR device 200 and the AR device 200 is being worn by a user such as medical personnel. As shown in FIG. 27, the medical personnel has donned a surgical gown 100 having a hood 102 and a face shield 374. As best shown in FIG. 26, the face shield 374 is located in close proximity to the center sensor array 206 so that the face shield 374 does not produce additional artifacts such as refractivity when the center sensor array 206 is being utilized.

Setting-Up the Various PPE Adapter Systems

In order to set-up each of the various PPE adapter systems 50, 50*b*, and 350 for use during surgical procedures, attention is directed to FIGS. 1-27. With respect to PPE adapter system 50*b*, attention is directed to FIGS. 1-8. In order to set up PPE adapter system 50*b*, as shown in FIGS. 3-6, sliding adapter mount 250 is attached to AR device 2*b* through the use of extension 264 and extension 255. The extension 264 is located within extension 255. The extension 255 is then removably attached to head band 20*b*.

A unique aspect of the present invention is the ability of the PPE adapter system 50*b* to be able to attach to a face shield 74 (FIGS. 3-6) and allow the AR device 2*b* to be rotated towards and away from face shield 74. In particular, as shown in FIGS. 3-6, a conventional face shield 74 can be attached to the PPE adapter system 50*b*. As discussed above, it is important to understand that in many medical procedures such as surgical procedures, a face shield 74 may be required to be worn by the medical personnel performing the surgical procedure. However, the present invention allows the AR device 2*b* to be tilted at an angle 76 with respect to the face shield 74. In this manner, PPE adapter system 50*b* is designed to rotate the AR device 2*b* in order to move the AR device 2*b* as close to the face shield 74, as possible. This is needed so the front camera 10*a* can calculate depth of objects without producing additional artifacts such as reflections. Furthermore, the tilt angle 76 of the face shield 74 should range between 5 and 15° with the preferable tilt angle 76 being 10° in order to allow the face shield 74 to be in close proximity to the front camera 10*a*.

Another unique aspect of the present invention is the use of sliding adapter 1300. In particular, as shown in FIGS. 4-6, the AR device 2*b* is rotated down for viewing and the sliding adapter 1300 is slid back towards the head band 20*b* so that the face shield 74 is located in close proximity to the front camera 10*a* (FIG. 6). In order to rotate the AR device 2*b* upwardly, as shown in FIG. 6, the release lever 1302 is lifted up and away from the plurality of stops 1304 and moved in the direction of arrow X. The release lever 1302 is then located within one of the desired plurality of stops 1304. The release lever 1302 allows the sliding adapter 1300 to move forward which then creates the clearance needed for the AR device 2*b* to be rotated upwardly and away from the user's face in order to allow the medical personnel to view the surgical field without the AR device 2*b* being in the visual field of the medical personnel.

Once the PPE adapter system 50*b* has been attached to AR device 2*b*, the user (such as a medical personnel) can then place the AR device 2*b*/PPE adapter system 50*b* on the user's head.

After the user has placed the AR device 2*b*/PPE adapter system 50*b* on the user's head, the user can then don the surgical gown 100. The surgical gown 100 can then be removably attached to the hood 102 at the face shield 74, as shown in FIGS. 7 and 8.

With respect to PPE adapter system 50, attention is directed to FIGS. 9-18. In order to set up PPE adapter system 50, as shown in FIGS. 10-12, bracket 62 is located over the mount 8. The channels 66 can also be located over headband 20. The PPE adapter system 50 can then be removably attached to the AR device 2 through the use of the threaded fasteners 60 and threaded fastener openings 18. The PPE adapter system 50 can be securely attached to the AR device 2 by placing the channels 66 over the headband 20 and attaching the threaded fasteners 60 to the threaded fastener openings 18. Conversely, the PPE adapter system 50 can be easily and quickly removed from the AR device 2 by removing the threaded fasteners 60 from the threaded fastener openings 18 and lifting the channels 66 off of headband 20 in the direction of arrows A.

Once the PPE adapter system 50 has been attached to AR device 2, the user (such as a medical personnel) can then place the AR device 2/PPE adapter system 50 on the user's head as shown in FIGS. 15 and 17.

After the user has placed the AR device 2/PPE adapter system 50 on the user's head, the user can then don the surgical gown 100. The surgical gown 100 can then be removably attached to the hood 102 at the face shield 74, as shown in FIGS. 16 and 18.

With respect to PPE adapter system 350, attention is directed to FIGS. 19-27. In order to set up PPE adapter system 350, as shown in FIGS. 22 and 23, primary interface clips 356 can be located over a portion of head band 208 adjacent to the direct view, transparent, liquid crystal displays 204 and secondary interface clips 358 can be located over end portions of head piece 210. The PPE adapter system 350 can then be removably attached to the AR device 200 through the use of the primary interface clips 356 and the secondary interface clips 358. The PPE adapter system 350 can be securely attached to the AR device 200 by having the primary interface clips 356 interact with and lock onto a portion of head band 208 adjacent to the direct view, transparent, liquid crystal displays 204 and secondary interface clips 358 interact with and lock onto the end portions of head piece 210. Conversely, the PPE adapter system 350 can be easily and quickly removed from the AR device 200 by removing the primary interface clips 356 from the portion of head band 208 adjacent to the direct view, transparent, liquid crystal displays 204 and removing the secondary interface clips 358 from the end portions of head piece 210.

Once the PPE adapter system 350 has been attached to AR device 200, the user (such as a medical personnel) can then place the AR device 200/PPE adapter system 350 on the user's head as shown in FIG. 27.

After the user has placed the AR device 200/PPE adapter system 350 on the user's head, the user can then don the surgical gown 100. The surgical gown 100 can then be removably attached to the hood 102 at the face shield 374, as shown in FIG. 27.

Operation of the Various PPE Adapter Systems

Another unique aspect of the present invention is the use of the various PPE adapter systems 50, 50*b*, and 350.

With respect to PPE adapter system 50*b*, attention is directed to FIGS. 7 and 8. Once the PPE adapter system 50*b* has been attached to AR device 2*b*, the user (such as a medical personnel) can then place the AR device 2*b*/PPE adapter system 50*b* on the user's head.

After the user has placed the AR device 2*b*/PPE adapter system 50*b* on the user's head, the user can then don the surgical gown 100. The surgical gown 100 can then be removably attached to the hood 102 at the face shield 74, as shown in FIGS. 7 and 8.

As discussed above, a unique aspect of the present invention is the ability of the PPE adapter system 50*b* to be able to attach to a face shield 74 (FIGS. 3-6) and allow the AR device 2*b* to be rotated towards face shield 74. In particular, as shown in FIGS. 2-5, a conventional face shield 74 can be attached to the PPE adapter system 50*b*. As discussed above, it is important to understand that in many medical procedures such as surgical procedures, a face shield 74 may be required to be worn by the medical personnel performing the surgical procedure. However, the present invention allows the AR device 2*b* to be tilted at an angle with respect to the face shield 74. In this manner, PPE adapter system 50*b* is designed to rotate the AR device 2*b* in order to move the AR device 2*b* as close to the face shield 74, as possible. This is needed so the front camera 10*a* can calculate depth of objects without producing additional artifacts such as reflections. Furthermore, the tilt angle 76 of the face shield 74 should range between 5 and 15° with the preferable tilt angle being 10° in order to allow the face shield 74 to be in close proximity to the front camera 10*a*.

Another unique aspect of the present invention is the use of sliding adapter 1300. In particular, as shown in FIGS. 3-6, the AR device 2*b* is rotated down for viewing and the sliding adapter 1300 is slid back towards the head band 20*b* so that the face shield 74 is located in close proximity to the front camera 10*a* (FIG. 6). In order to rotate the AR device 2*b* upwardly, as shown in FIG. 6, the release lever 1302 is lifted up and away from the plurality of stops 1304 and moved in the direction of arrow X. The release lever 1302 is then located within one of the desired plurality of stops 1304. The movement of the release lever 1302 causes the AR device 2*b* to be rotated up and away from the face shield 74 in order to allow the medical personnel to view the surgical field without the AR device 2*b* being in the visual field of the medical personnel (FIG. 8). Preferably, the total travel length of the release lever 302 is approximately 50 mm.

A still another unique aspect of the present invention is the use of hook and loop fasteners 72*b* located around a periphery of wall 54*b*. Preferably, hook and loop fasteners 72*b* are constructed in a similar manner as hook and loop fasteners 72. The unique aspect of use of the hook and loop fasteners 72*b* is that the hook and loop fasteners 72*b* allow the PPE adapter system 50*b* to be removably attached to the face shield 74 (FIGS. 3-5). In this manner, the once the PPE adapter system 50*b* has been removably attached to AR device 2*b* and the AR device 2*b* has been placed on the head of the medical personnel, the surgical gown 100 can be located over the medical personnel and the hood 102 can be securely attached to the PPE adapter system 50*b* so that the face shield 74 and hood 102 remain in place on the medical personnel, especially during the medical procedure. As shown in FIGS. 7 and 8, the hook and loop fasteners 72*b* can be attached to the hood at a location along a top edge of the face shield 74.

With respect to PPE adapter system 50, attention is directed to FIGS. 15-18. As discussed above, once the PPE adapter system 50 has been attached to AR device 2, the user (such as a medical personnel) can then place the AR device 2/PPE adapter system 50 on the user's head as shown in FIGS. 15 and 17.

After the user has placed the AR device 2/PPE adapter system 50 on the user's head (FIGS. 15 and 17), the user can then don the surgical gown 100. The surgical gown 100 can then be removably attached to the hood 102 at the face shield 74, as shown in FIGS. 16 and 18.

As discussed above, another unique aspect of the present invention is the ability of the PPE adapter system 50 to be able to attach to a face shield 74 (FIGS. 13 and 14). In particular, as shown in FIGS. 13 and 14, a conventional face shield 74 can be attached to the PPE adapter system 50. It is important to understand that in many medical procedures such as surgical procedures, a face shield 74 may be required to be worn by the medical personnel performing the surgical procedure. However, the present invention allows the face shield 74 to be tilted at an angle 76 with respect to the front camera 10. In this manner, PPE adapter system 50 is designed to have a forward tilt in order to move the face shield 74 as close to the front camera 10, as possible. This is needed so the front camera 10 can calculate depth of objects without producing additional artifacts such as reflections. Furthermore, the tilt angle 76 of the face shield 74 should range between 5 and 15° with the preferable tilt angle being 10° in order to allow the face shield 74 to be in close proximity to the front camera 10.

A still another unique aspect of the present invention is the use of hook and loop fasteners 72 located around a periphery of wall 54. Preferably, hook and loop fasteners 72 are constructed of Velcro® or any other similar hook and loop material. The unique aspect of use of the hook and loop fasteners 72 is that the hook and loop fasteners 72 allow the PPE adapter system 50 to be removably attached to the face shield 74 (FIGS. 13 and 14). In this manner, the once the PPE adapter system 50 has been removably attached to AR device 2 and the AR device 2 has been placed on the head of the medical personnel, the surgical gown 100 can be located over the medical personnel and the hood 102 can be securely attached to the PPE adapter system 50 so that the 74 and face shield hood 102 remain in place on the medical personnel, especially during the medical procedure. As shown in FIGS. 13 and 14, the hook and loop fasteners 72 can be attached to the hood at a location along a top edge of the face shield 74.

With respect to PPE adapter system 350, attention is directed to FIG. 27. As discussed above, once the PPE adapter system 350 has been attached to AR device 200, the user (such as a medical personnel) can then place the AR device 200/PPE adapter system 350 on the user's head as shown in FIG. 27.

After the user has placed the AR device 200/PPE adapter system 350 on the user's head, the user can then don the surgical gown 100. The surgical gown 100 can then be removably attached to the hood 102 at the face shield 374, as shown in FIG. 27.

While the disclosed embodiments have been illustrated and described in considerable detail, it is not the intention to restrict or in any way limit the scope of the appended claims to such detail. It is, of course, not possible to describe every conceivable combination of components or methodologies for purposes of describing the various aspects of the subject matter. Therefore, the disclosure is not limited to the specific details or the illustrative examples shown and described. Thus, this disclosure is intended to embrace alterations, modifications, and variations that fall within the scope of the appended claims, which satisfy the statutory subject matter requirements of 35 U.S.C. § 101.

To the extent that the term "includes" or "including" is employed in the detailed description or the claims, it is intended to be inclusive in a manner similar to the term "comprising" as that term is interpreted when employed as a transitional word in a claim.

To the extent that the term "or" is used in the detailed description or claims (e.g., A or B) it is intended to mean "A or B or both". When the applicants intend to indicate "only A or B but not both" then the phrase "only A or B but not both" will be used. Thus, use of the term "or" herein is the inclusive, and not the exclusive use.

Therefore, provided herein is a new and improved PPE adapter system for use with use with AR devices and lighting devices, according to various embodiments of the present invention, offers the following advantages: ease of use; lightness in weight; the ability to use the AR device in conjunction with a face shield; the ability to use the adapter system on a variety of AR devices; portability; ease of attachment of the adapter to the AR device; ease of removal of the adapter from the AR device; and reduced cost. In fact, in many of the preferred embodiments, these advantages of ease of use, lightness in weight, the ability to use the AR device and/or lighting device in conjunction with a face shield, the ability to use the adapter system on a variety of AR and/or lighting devices, portability, ease of attachment of the adapter to the AR and/or lighting device, ease of removal of the adapter from the AR and/or lighting device, and reduced cost are optimized to an extent that is considerably higher than heretofore achieved in prior, known systems and methods for employing a spatial imaging system and/or a light system with PPE during a medical procedure.

What is claimed is:

1. A personal protective equipment ("PPE") adapter system for use with an augmented reality ("AR") device, comprising:

an AR device having a front camera and a headband connected to the AR viewing display;

a slidable PPE adapter system connected to the headband, wherein the PPE adapter system further comprises;

a sliding adapter mount configured to be removably attached to the AR device and the face shield, wherein the sliding adapter amount includes a first extension having an opening and a wall, a sliding adapter carrier configured to be removably attached to the first extension, wherein the sliding adapter carrier includes a second extension that is configured to be located within the first extension, and a sliding adapter configured to be removably attached to the sliding adapter carrier and the sliding adapter is also configured to assist in rotating the AR device towards and away from the face shield; and a PPE hood connected to the PPE adapter system, wherein the PPE hood includes a face shield, wherein the face shield is removably connected to the PPE adapter system.

2. The personal protective equipment ("PPE") adapter system, according to claim 1, wherein the sliding adapter further comprises:

a sliding adapter lever holder;

a release lever connected to the sliding adapter lever holder; and a plurality of lever stops located adjacent to the release lever.

3. The personal protective equipment ("PPE") adapter system, according to claim 1, wherein the PPE adapter system further comprises: a hook and loop fastener located along a portion of the wall on the sliding adapter mount, wherein the hook and loop fastener is removably connected to the face shield.

4. The personal protective equipment ("PPE") adapter system, according to claim 1, wherein the PPE adapter system is constructed of a durable, UV resistant, heat resistant, lightweight, high strength polymeric material.

5. The personal protective equipment ("PPE") adapter system, according to claim 1, wherein the face shield is configured to be located within close proximity to the front camera.

6. A personal protective equipment ("PPE") adapter system for use with an augmented reality ("AR") device, comprising:

an AR device having a computer module, a head gear, a front camera, an AR viewing display, and a headband, wherein the AR device further comprises;

a mount located adjacent to the front camera, wherein the mount is configured for assisting in mounting the PPE adapter system to the AR device, and a plurality of threaded openings located on the mount;

a PPE adapter system operatively connected to the AR device; and a PPE hood operatively connected to the PPE adapter system, wherein the PPE hood includes a face shield, wherein the face shield is removably connected to the PPE adapter system.

7. The personal protective equipment ("PPE") adapter system, according to claim 6, wherein the PPE adapter system further comprises:

a first wall;

an extension connected at one end to the first wall;

a second wall connected at the other end of the extension;

a plurality of channels connected to the second wall, wherein each of the plurality of channels is configured to be attached to a portion of the headband; and a bracket located between the plurality of channels, wherein the bracket includes a bracket opening and wherein the bracket is configured to be attached to the mount at the bracket opening through the use of a plurality of threaded fasteners and the plurality of threaded openings.

8. The personal protective equipment ("PPE") adapter system, according to claim 6, wherein the PPE adapter system further comprises:

a hook and loop fastener located along a portion of the first wall, wherein the hook and loop fastener is removably connected to the face shield.

9. The personal protective equipment ("PPE") adapter system, according to claim 7, wherein the PPE adapter system further comprises:

a plurality of openings located in the extension, wherein the plurality of openings is configured to allow for air to circulate within the PPE hood.

10. The personal protective equipment ("PPE") adapter system, according to claim 6, wherein the face shield is configured to be located within close proximity to the front camera.

11. A personal protective equipment ("PPE") adapter system for use with an augmented reality ("AR") device, comprising:

an AR device having a plurality of side sensor arrays, a plurality of direct view, transparent, liquid crystal displays located adjacent to the plurality of side sensor arrays, a center sensor array located adjacent to each of the plurality of direct view, transparent, liquid crystal displays, and a headband, wherein the AR device further comprises;

a head piece located adjacent to the center sensor array, wherein the head piece is configured for assisting in mounting the PPE adapter system to the AR device, a wall, a first extension connected at one end to the wall, a plurality of second extensions, wherein each of the plurality of second extensions is connected at one end to the first extension, a plurality of primary interface clips, wherein each of the plurality of primary interface clips is connected at another end of each of the plurality of second extensions and wherein each of the plurality primary interface clips is configured to be removably attached to a portion of the headband, and a plurality of secondary interface clips, wherein each of the plurality of secondary interface clips is connected to one of the plurality of primary interface clips and wherein each of the plurality of secondary interface clips is configured to be removably attached to the head piece;

a PPE adapter system operatively connected to the AR device; and a PPE hood operatively connected to the PPE adapter system, wherein the PPE hood includes a face shield, wherein the face shield is removably connected to the PPE adapter system.

12. The personal protective equipment ("PPE") adapter system, according to claim 11, wherein the PPE adapter system further comprises:

a hook and loop fastener located along a portion of the wall, wherein the hook and loop fastener is removably connected to the face shield.

13. The personal protective equipment ("PPE") adapter system, according to claim 11, wherein the PPE adapter system further comprises:

a plurality of first openings located in portions of the first extension; and a plurality of second openings, wherein each of the plurality of second openings is located on each of the plurality second extensions and wherein the plurality of first and second openings are configured to allow for air to circulate within the PPE hood.

14. The personal protective equipment ("PPE") adapter system, according to claim 11, wherein the PPE adapter system further comprises:

a bracket located between the plurality of primary interface clips; and a light mounting bar connected to a portion of the bracket.

15. The personal protective equipment ("PPE") adapter system, according to claim 11, wherein the face shield is configured to be located within close proximity to the center sensor array.

16. The personal protective equipment ("PPE") adapter system, according to claim 11, wherein the face shield further comprises:

a first curved portion;

a flat portion located to the first curved portion, wherein the flat portion is configured to be located adjacent to the center sensor array; and a second curved portion located adjacent to the flat portion.

* * * * *